United States Patent [19]

Johnston et al.

[11] Patent Number: 5,451,416
[45] Date of Patent: * Sep. 19, 1995

[54] NONDIGESTIBLE FAT COMPOSITIONS CONTAINING COCRYSTALLIZED BLEND OF POLYOL POLYESTER HARDSTOCK AND CRYSTAL MODIFIER AS A PASSIVE OIL LOSS CONTROL AGENT

[76] Inventors: Robert W. Johnston; Peter Y. T. Lin; Michael L. Mead, all of The Procter & Gamble Co., 6071 Center Hill Ave. - F3A22, Cincinnati, Ohio 45224-1703

[ * ] Notice: The portion of the term of this patent subsequent to Jun. 6, 2012 has been disclaimed.

[21] Appl. No.: 287,976

[22] Filed: Aug. 10, 1994

Related U.S. Application Data

[63] Continuation-in-part of Ser. No. 969,607, Oct. 30, 1992, abandoned.

[51] Int. Cl.$^6$ ................................................. A23L 1/00
[52] U.S. Cl. ................................. 426/531; 426/601; 426/611; 426/804; 536/119; 554/227
[58] Field of Search ............... 426/438, 531, 549, 601, 426/606, 607, 609, 610, 611, 612, 804; 536/119; 554/161, 227

[56] References Cited

U.S. PATENT DOCUMENTS

| | | | |
|---|---|---|---|
| 2,097,720 | 11/1937 | Clayton et al. | 260/398.5 |
| 2,266,591 | 12/1941 | Eckey et al. | 99/163 |
| 2,962,419 | 11/1960 | Minich | 167/81 |
| 3,059,009 | 10/1962 | Schmid et al. | 260/428 |
| 3,059,010 | 10/1962 | Shcmid et al. | 260/428 |
| 3,093,481 | 6/1963 | Eckey et al. | 99/118 |
| 3,158,490 | 11/1964 | Baur et al. | 99/118 |
| 3,353,966 | 11/1967 | Hugenberg et al. | 99/163 |
| 3,353,967 | 11/1967 | Lutton | 99/163 |
| 3,360,376 | 12/1967 | Dobson | 99/118 |
| 3,367,782 | 2/1968 | Lutton et al. | 99/118 |
| 3,397,997 | 8/1968 | Japikse | 99/118 |
| 3,443,966 | 5/1969 | Reid | 99/118 |
| 3,495,010 | 2/1970 | Fossel | 424/312 |
| 3,495,011 | 2/1970 | Fossel | 424/312 |
| 3,600,186 | 8/1971 | Mattson et al. | 99/1 |
| 3,637,774 | 1/1972 | Babayan et al. | 260/410.6 |
| 3,649,647 | 3/1972 | Ota | 260/345.8 |
| 4,005,195 | 1/1977 | Jandacek | 424/180 |
| 4,005,196 | 1/1977 | Jandacek et al. | 424/180 |
| 4,363,763 | 12/1982 | Peterson | 260/410.7 |
| 4,368,213 | 1/1983 | Hollenbach et al. | 426/590 |
| 4,469,635 | 9/1984 | Peterson | 260/403 |
| 4,582,715 | 4/1986 | Volpenhein | 426/601 |
| 4,797,300 | 1/1989 | Jandacek et al. | 426/549 |
| 4,830,787 | 5/1989 | Klemann | 260/410 |
| 4,919,964 | 4/1990 | Adams et al. | 426/564 |
| 4,959,465 | 9/1990 | Klemann | 536/115 |
| 4,960,602 | 10/1990 | Talkington et al. | 426/534 |
| 4,962,092 | 10/1990 | Wood | 514/23 |
| 4,963,386 | 10/1990 | Klemann | 426/611 |
| 4,980,191 | 12/1990 | Christensen | 426/601 |
| 5,017,398 | 5/1991 | Jandacek et al. | 426/603 |
| 5,085,884 | 2/1992 | Young et al. | 426/611 |
| 5,102,683 | 4/1992 | Letton et al. | 426/601 |
| 5,137,743 | 8/1992 | Zaks et al. | 426/602 |

(List continued on next page.)

FOREIGN PATENT DOCUMENTS 233856 8/1987 European Pat. Off. .
236288 9/1987 European Pat. Off. .

(List continued on next page.)

Primary Examiner—Leslie A. Wong
Attorney, Agent, or Firm—Tara M. Rosnell; G. W. Allen; Rose Ann Dabek

[57] ABSTRACT

Nondigestible fat compositions having relatively flat Solid Fat Content (SFC) profile slopes between typical room and body temperatures are disclosed. These nondigestible fat comprise a liquid nondigestible oil and relatively small nondigestible particles dispersed in the oil to control passive oil loss. These nondigestible particles consist essentially of a cocrystallized blend of a nondigestible solid polyol fatty acid polyester hardstock and a crystal modifier capable of inducing this hardstock to form these relatively small particles. Edible fat-containing products comprising these nondigestible fat can be less waxy tasting due to the lower level of solids required for passive oil loss control.

25 Claims, 5 Drawing Sheets

U.S. PATENT DOCUMENTS

| | | |
|---|---|---|
| 5,158,796 | 10/1992 | Bernhardt et al. ............... 426/549 |
| 5,194,270 | 3/1993 | Cante et al. ..................... 426/74 |
| 5,219,604 | 6/1993 | Klemann et al. ................. 426/531 |
| 5,225,049 | 7/1993 | Barmentlo et al. ............... 203/34 |
| 5,230,913 | 7/1993 | Klemann ......................... 426/97 |
| 5,236,733 | 8/1993 | Zimmerman et al. ............ 426/611 |
| 5,306,514 | 4/1994 | Letton et al. .................... 426/531 |
| 5,306,515 | 4/1994 | Letton et al. .................... 426/531 |
| 5,306,516 | 4/1994 | Letton et al. .................... 426/531 |
| 5,308,708 | 5/1994 | Baer et al. ....................... 426/611 |
| 5,338,564 | 8/1994 | Meyer et al. .................... 426/612 |

FOREIGN PATENT DOCUMENTS

| | | |
|---|---|---|
| 311154 | 4/1989 | European Pat. Off. . |
| 0325463 | 7/1989 | European Pat. Off. . |
| 350987 | 1/1990 | European Pat. Off. . |
| 375027 | 6/1990 | European Pat. Off. . |
| 390410 | 10/1990 | European Pat. Off. . |
| 420314 | 4/1991 | European Pat. Off. . |
| 424066 | 4/1991 | European Pat. Off. . |
| 434117 | 6/1991 | European Pat. Off. . |
| 434119 | 6/1991 | European Pat. Off. . |
| 207070 | 2/1984 | Germany . |
| 227137 | 9/1985 | Germany . |
| 49-26220 | 3/1974 | Japan . |
| 52-27694 | 7/1977 | Japan . |
| 58-78531 | 5/1983 | Japan . |
| 9062511A | 4/1984 | Japan . |
| 59-143550 | 8/1984 | Japan . |
| 59-156242 | 9/1984 | Japan . |
| 2020247A | 1/1990 | Japan . |
| 2-262538 | 10/1990 | Japan . |
| 92193361 | 6/1992 | Japan . |
| 3-81042 | 8/1992 | Japan . |
| 04237458A | 8/1992 | Japan . |
| WO91/10368 | 7/1991 | WIPO . |
| WO91/15961 | 10/1991 | WIPO . |
| WO91/15962 | 10/1991 | WIPO . |
| WO91/15963 | 10/1991 | WIPO . |
| WO92/03937 | 3/1992 | WIPO . |
| WO92/04360 | 3/1992 | WIPO . |
| WO92/17077 | 10/1992 | WIPO . |
| WO91/15960 | 10/3191 | WIPO . |

NONDIGESTIBLE FAT COMPOSITIONS CONTAINING COCRYSTALLIZED BLEND OF POLYOL POLYESTER HARDSTOCK AND CRYSTAL MODIFIER AS A PASSIVE OIL LOSS CONTROL AGENT

This is a continuation-in-part of application Ser. No. 07/969,607, filed on Oct. 30, 1992, now abandoned.

TECHNICAL FIELD

The present invention relates to nondigestible fat compositions that are useful as full or partial replacers for triglyceride fats or oils in foods. More particularly, the present invention provides such nondigestible fat compositions that provide passive oil loss control without being excessively waxy tasting.

BACKGROUND OF THE INVENTION

Certain polyol fatty acid polyesters have been suggested as low or reduced calorie substitutes for triglyceride fats and oils used in foods. For example, nonabsorbable, nondigestible sugar fatty acid esters or sugar alcohol fatty acid esters having at least 4 fatty acid ester groups with each fatty acid having from 8 to 22 carbon atoms have been used as partial or full fat replacers in low calorie food compositions. (See Mattson & Volpenhein; U.S. Pat. No. 3,600,186; Issued Aug. 17, 1971.) Foods in which these polyol polyesters are particularly useful as partial or complete replacements for triglyceride fats or oils include products suitable for use in frying. Unfortunately, regular ingestion of moderate to high levels of completely liquid forms of these polyol polyesters can produce undesirable passive oil loss, namely, leakage of the polyesters through the anal sphincter. By contrast, completely solid versions of these polyesters provide a sufficiently high solids content at mouth temperatures (e.g., 92° F., 33.3° C.) such that they give a waxy taste or impression in the mouth when ingested.

As an alternative to these completely liquid or completely solid nondigestible/nonabsorbable polyol polyesters, certain intermediate melting polyol fatty acid polyesters have been developed that provide passive oil loss control, while at the same time reducing waxiness in the mouth. (See Bernhardt; European Patent Application Nos. 236,288 and 233,856; Published Sep. 9, and Aug. 26, 1987, respectively.) These intermediate melting polyol polyesters exhibit a unique rheology at body temperature by virtue of their having a matrix which involves a minimal level of solids (e.g. about 12% or lower) that bind the remaining liquid portion. As a result, these intermediate melting polyol polyesters are sufficiently viscous and have a sufficiently high liquid/solid stability at body temperature to provide passive oil loss control. An example of such intermediate melting polyol polyesters are those obtained by substantially completely esterifying sucrose with a 55:45 mixture of fully hydrogenated (hardstock) and partially hydrogenated soybean oil fatty acid methyl esters. (See Examples 1 and 2 of the above European patent applications.)

These intermediate melting polyol polyesters can be used as total or partial replacements for other fats and oils in various food products, including cooking and frying oils. However, it has been found that certain foods such as potato chips fried in frying fats containing substantial levels of these nondigestible intermediate melting polyol polyesters, particularly at levels in excess of about 40%, can give a significantly increased waxiness impression compared to potato chips that have been fried in the digestible triglyceride fat or oil that the nondigestible polyol polyester has partially replaced. (In terms of physical properties, "waxiness" relates to how the fat composition is sensed in the mouth, and specifically relates in part to the sensation of the product having a relatively high level of solids.) Indeed, this increased waxiness impression with regard to these intermediate melting polyol polyesters is recognized in the aforementioned European Patent Application No. 233,856 in as much as that application discloses fat compositions which contain digestible food materials, such as triglycerides and substituted mono- and diglycerides, that act as solvents for the intermediate melting polyol polyesters. However, as the proportion of triglycerides is increased relative to the intermediate melting polyol polyesters so as to impart less waxiness, the caloric content of the frying fat also increases accordingly. In addition, it has been found that frying fats containing greater than about 40% of these intermediate melting polyol polyesters can adversely affect the flavor display of the resulting fried food, in particular potato chips.

The waxiness impression imparted by intermediate melting polyol polyesters such as those of the aforementioned European '288 and '856 applications is believed to be due at least in part to their change in Solid Fat Content (SFC), particularly between typical room temperature (i.e. 70° F., 21.1° C.) and body temperature (i.e. 98.6° F., 37° C.). For example, the intermediate melting sucrose polyester of Example 2 of European Patent Application Nos. 233,856 and 236,128 has an SFC profile slope (as hereinafter defined) between room temperature and body temperature of about −1.3. In other words, the SFC profile slope of these intermediate melting polyol polyesters is relatively steep. Given this relatively steep SFC profile slope, the change in solids content of these intermediate melting polyol polyesters can be sufficiently great such that a high level of solids will be sensed when such room temperature materials are first placed in the mouth, thereby leading to an increased waxiness sensation.

Blends of completely liquid polyol polyesters with completely solid polyol polyester hardstocks, preferably esterified with $C_{10}$-$C_{22}$ saturated fatty acids (e.g. sucrose octastearate), have also been proposed in order to provide passive oil loss control. (See, for example, Jandacek; U.S. Pat. No. 4,005,195; and Jandacek/Mattson; U.S. Pat. No. 4,005,196; Both issued Jan. 25, 1977.) Blends of these liquid polyol polyesters and solid polyol polyesters hardstocks have relatively flat SFC profile slopes between typical room temperature and body temperature, i.e. slopes of from 0 to about −0.3, and more typically from 0 to about −0.1. In other words, there is little or no change in the solids content of these blends between room temperature and body temperature.

Although providing at least temporary passive oil loss control, blends of liquid polyol polyesters and solid polyol polyester hardstocks according to the aforementioned U.S. '195 and '196 patents do not necessarily provide passive oil loss control over an extended period of time. It has been found that these solid polyol polyester hardstocks normally tend to form large spherulitic particles (typically from about 3 to about 32 microns in size) in the liquid polyol polyesters. These large spherulitic particles may tend to phase separate from the liquid polyol polyesters during storage of such blends. As a result, a two-phase system can develop with the liquid portion thereof providing minimal or no passive oil loss control.

In addition, blends of liquid polyol polyesters and solid polyol polyester hardstocks according to the aforementioned U.S. Pat. Nos. 4,005,195 and 4,005,196 do not necessarily lead to less waxy tasting products. As taught in these patents, a relatively high level of solid polyol polyester hardstock is required to provide passive oil loss control. For example, hardstock is preferably used in an amount of from about 20% to about 50% by weight of the liquid polyol polyester. (See Column 9, lines 65–68, of U.S. Pat. No. 4,005,195.) Such a level of solid polyol polyester hardstock used for passive oil loss control at body temperature can lead to a waxy tasting product due to the relatively high level of solids that will also be present at mouth temperature.

In view of the foregoing, it would be desirable to provide nondigestible fat compositions comprising blends of liquid polyol polyesters and solid polyol polyester hardstock particles with such blends exhibiting little or no phase separation of the hardstock particles from the liquid polyol polyesters. In addition, it would be desirable to be able to reduce the level of solid polyol polyester hardstock required for effective passive oil loss control so as to provide less waxy tasting products.

In addition to being useful as passive oil loss control agents when combined with liquid nondigestible oils, certain polyol polyesters which are solid at temperatures of about 25° C. and higher have also been used as thickening agents for conventional digestible triglyceride oils. For example, these solid polyol polyesters have been used as "thickening agents" for blending with liquid digestible or nondigestible oils in formulations such as shortenings, as well as in other food products which contain a combination of fat and nonfat ingredients, e.g., margarines, mayonnaise, frozen dairy desserts and the like. (See, for example, Jandacek and Letton; U.S. Pat. No. 4,797,300; Issued Jan. 10, 1989.) However, these prior art thickening agents had to be used at levels of 10% to 25%. Accordingly, it would also be desirable to reduce the level of thickening agents in formulations of this type in order to provide less waxy tasting products.

SUMMARY OF THE INVENTION

The present invention relates to nondigestible fat compositions which are useful as replacements for triglyceride fats and oils in food products. Such compositions have a Solid Fat Content (SFC) profile slope between room temperature (70° F., 21° C.) and body temperature (98.6° F., 37° C.) of from 0 to about $-0.75\%$ solids/°F. Such compositions further comprise a liquid nondigestible oil component having dispersed therein nondigestible solid polyol polyester particles in an amount sufficient to control passive oil loss upon the ingestion of the nondigestible fat compositions.

The liquid nondigestible oil component of the compositions herein is one which has a complete melting point below about 37° C. The solid polyol polyester particles of the composition herein have a complete melting point above about 37° C. and further have a thickness of about 1 micron or less.

The nondigestible passive oil loss particles furthermore consist essentially of a cocrystallized blend of
(a) a nondigestible solid polyol polyester hardstock having a complete melting point above about 37° C. and normally tending to form spherulitic particles having a diameter of about 3 microns or larger when crystallized in the liquid nondigestible oil; and
(b) a crystal modifier capable of inducing the hardstock to form nondigestible particles having a thickness of about 1 micron or less when cocrystallized with the hardstock in the nondigestible oil.

The ratio of the hardstock to the crystal modifier in the cocrystallized blend ranges from about 99.9:0.1 to about 20:80.

The present invention also relates to a process for preparing these nondigestible fat compositions. This process comprises the steps of:
(I) forming a melted mixture comprising the liquid nondigestible oil and a cocrystallizable blend consisting essentially of the nondigestible polyol polyester hardstock and the crystal modifier component as hereinbefore described, and thereafter,
(II) cooling the melted mixture formed from step (I) in a manner such that the cocrystallizable blend forms, in the oil, dispersed nondigestible passive oil loss control particles having a thickness of about 1 micron or less.

The nondigestible fat compositions of the present invention provide significant advantages over known intermediate melting polyol polyesters, as well as prior art blends of liquid polyol polyester and solid polyol polyester hardstocks. The relatively small nondigestible particles provide especially efficient passive oil loss control. As a result, the level of solids at body temperature required for passive oil loss control can be reduced to relatively low levels, (e.g., to less than 20%, preferably to less than 15% of the nondigestible fat). In addition, the nondigestible fats of the present invention have relatively flat SFC profile slopes, thus leading to minimal or no change in solids content between typical room and body temperature. This combination of relatively low solids levels required for passive oil loss control, with minimal/no solids content change between room and body temperatures, can result in less waxy tasting products containing these nondigestible fats.

The present invention also relates to digestible fat compositions which utilize particles of the hereinbefore described nondigestible polyol polyester material as thickening agents. Such compositions comprise from about 85% to about 98% of a digestible edible oil and from about 2% to about 15% of the nondigestible solid polyol polyester particles.

DETAILED DESCRIPTION OF THE INVENTION

I. Definitions

Figure 1A:
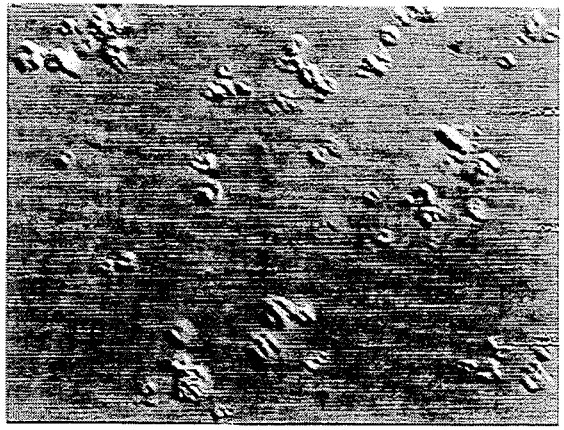
FIGS. 1A through 1D are photomicrographs (magnification of 1,000x) of nondigestible fat compositions comprising a liquid sucrose polyester and a solid sucrose polyester hardstock at total solids levels of 1%, 3%, 6% and 9%, respectively.
Figure 1B:
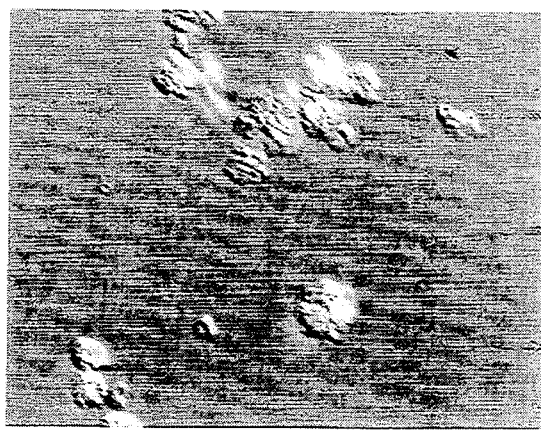
Figure 1C:
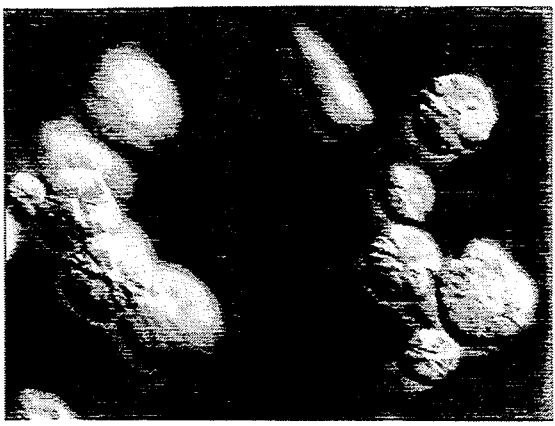
Figure 1D:

By "nondigestible" is meant that only about 70% or less of the material can be digested by the body. Preferably, only about 20% or less of such materials can be digested. More preferably, only about 1% or less of such materials can be digested.

As used herein, the term "thickness" of a particle is used in its conventional sense of the smallest of the three dimensions (length, width, height) of any given particle.

As used herein, the term "spherulitic" refers to substantially spherical or round, essentially three-dimensional particles.

As used herein, the term "platelet-like" refers to a substantially flat, essentially two-dimensional type of particle having length and width in the unfolded planar configuration that is substantially greater in dimension than its thickness.

As used herein, the terms "filament-like" and "rod-like" refer to elongated, essentially one-dimensional particles.

As used herein, the term "complete melting point" refers to the temperature at which all solid components have melted. All melting points referred to herein are measured by Differential Scanning Calorimetry (DSC) as described hereinafter.

As used herein, the term "crystallization temperature" refers to the temperature at which solid crystalline particles begin to form from the liquid phase.

As used herein, the terms "cocrystallizable blend" and "cocrystallizable particles" refer to blends or particles wherein a polyol polyester hardstock and a crystal modifier crystallize from a liquid phase at the same time, i.e. the components of the blend or particles have similar crystallization temperatures or the crystallization temperatures are such that the hardstock and crystal modifier will crystallize simultaneously.

As used herein, the term "comprising" means various components, or steps, can be conjointly employed in the nondigestible fat compositions and processes of the present invention. Accordingly, the term "comprising" encompasses the more restrictive terms "consisting essentially of" and "consisting of".

By "polyol" is meant a polyhydric alcohol containing at least 4, preferably from 4 to 12, more preferably from 4 to 8, most preferably from 6 to 8, hydroxyl groups. Polyol thus include sugars (i.e., monosaccharides, disaccharides and trisaccharides), sugar alcohols (i.e., the reduction product of sugars wherein the aldehyde or ketone group has been reduced to an alcohol), other sugar derivatives (e.g., alkyl glycosides), polyglycerols such as diglycerol and triglycerol, pentaerythritol, and polyvinyl alcohols. Specific examples of suitable sugars, sugar alcohols and sugar derivatives include xylose, arabinose, ribose, xylitol, erythritol, glucose, methyl glucoside, mannose, galactose, fructose, sorbitol, maltose, lactose, sucrose, raffinose, and maltotriose. Preferred polyols include erythritol, xylitol, sorbitol, and glucose, with sucrose being an especially preferred polyol.

By "polyol polyester" is meant a polyol as hereinbefore described having at least 4 ester groups, i.e., at least 4 of the hydroxyl groups are esterified with fatty or other organic acids. Polyol esters that contain 3 or less ester groups are digested in (and the products of digestion are absorbed from) the intestinal tract much in the manner of ordinary triglyceride fats or Oils, whereas those polyol esters which contain 4 or more ester groups are generally substantially nondigestible and consequently nonabsorbable by the human body. It is not necessary that all of the hydroxyl groups of the polyol be esterified, but it is preferable that disaccharide molecules contain no more than 3 unesterified hydroxyl groups, and more preferably no more than 2 unesterified hydroxyl groups, so that they are rendered nondigestible. Typically, substantially all (e.g., at least about 85%) of the hydroxyl groups of the polyol are esterified. For liquid polyol polyesters, preferably at least about 95% of the hydroxyl groups of the polyol are esterified. In the case of sucrose polyesters, typically from about 7 to 8 of the hydroxyl groups of the polyol are esterified.

By "ester group" is meant a moiety formed from the reaction of a hydroxyl group with an organic acid or acid derivative which moiety contains fatty acid and/or other organic radicals having at least 2 carbon atoms, typically at least 8 carbon atoms, more typically at least 12 carbon atoms, and most typically at least 16 carbon atoms. Representative examples of such fatty acid and other organic acid radicals include acetic, propionic, butyric, caprylic, capric, lauric, myristic, myristoleic, palmitic, palmitoleic, stearic, oleic, elaidic, ricinoleic, linoleic, linolenic, eleostearic, arachidic, arachidonic, behenic, lignoceric, erucic, and cerotic fatty acid radicals and other organic acid radicals including aromatic esters-forming radicals such as benzoic or toluic; branched chain radicals such as isobutyric, neooctanoic or methyl stearic; ultra-long chain saturated or unsaturated fatty acid radicals such as tricosanoic or triconsenoic; cyclic aliphatics such as cyclohexane carboxylic; and polymeric ester-forming radicals such as polyacrylic and dimer fatty acid. The fatty or other organic acid radicals can be derived from naturally occurring or synthetic fatty acids. The acid radicals can be saturated or unsaturated, including positional or geometric isomers, e.g. cis- or trans-isomers, straight chain or branched aromatic or aliphatic, and can be the same for all ester groups, or can be mixtures of different acid radicals.

All percentages, ratios and proportions used herein are by weight unless otherwise specified.

II) Liquid Nondigestible Oil

A key component of the nondigestible fat compositions herein is a liquid nondigestible oil having a complete melting point below about 37° C. Suitable liquid nondigestible edible oils for use herein include liquid polyol polyesters (see Jandacek; U.S. Pat. No. 4,005,195; Issued Jan. 25, 1977); liquid esters of tricarballytic acids (see Harem; U.S. Pat. No. 4,508,746; Issued Apr. 2, 1985); liquid diesters of dicarboxylic acids such as derivatives of malonic and succinic acid (see Fulcher; U.S. Pat. No. 4,582,927; Issued Apr. 15, 1986); liquid triglycerides of alpha-branched chain carboxylic acids (see Whyte; U.S. Pat. No. 3,579,548; Issued May 18, 1971); liquid ethers and ether esters containing the neopentyl moiety (see Minich; U.S. Pat. No. 2,962,419; Issued Nov. 29, 1960); liquid fatty polyethers of polyglycerol (See Hunter et al; U.S. Pat. No. 3,932,532; Issued Jan. 13, 1976); liquid alkyl glycoside fatty acid polyesters (see Meyer et al; U.S. Pat. No. 4,840,815; Issued Jun. 20, 1989); liquid polyesters of two ether linked hydroxypolycarboxylic acids (e.g., citric or isocitric acid) (see Huhn et al; U.S. Pat. No. 4,888,195; Issued Dec. 19, 1988); liquid esters of epoxide-extended polyols (see White et al; U.S. Pat. No. 4,861,613; Issued Aug. 29, 1989); as well as liquid polydimethyl siloxanes (e.g., Fluid Silicones available from Dow Corning). All of the foregoing patents relating to liquid nondigestible oils are incorporated herein by reference.

Preferred liquid nondigestible oils are the liquid polyol polyesters that comprise liquid sugar polyesters, liquid sugar alcohol polyesters, and mixtures thereof. The preferred sugars and sugar alcohols for preparing these liquid polyol polyesters include erythritol, xylitol, sorbitol, and glucose, with sucrose being especially preferred. The sugar or sugar alcohol starting materials for these liquid polyol polyesters are preferably esterified with fatty acids containing from 8 to 22 carbon atoms, and most preferably from 8 to 18 carbon atoms. Suitable naturally occurring sources of such fatty acids include corn oil fatty acids, cottonseed oil fatty acids, peanut oil fatty acids, soybean oil fatty acids, canola oil fatty acids (i.e. fatty acids derived from low erucic acid rapeseed oil), sunflower seed oil fatty acids, sesame seed oil fatty acids, safflower oil fatty acids, fractionated palm oil fatty acids, palm kernel oil fatty acids, coconut oil fatty acids, tallow fatty acids and lard.

The nondigestible polyol polyesters that are liquid are those which have minimal or no solids at body temperatures (i.e., 98.6° F., 37° C.). These liquid polyol polyesters typically contain ester groups having a high proportion of $C_{12}$ or lower fatty acid radicals or else a high proportion of $C_{18}$ or higher unsaturated fatty acid radicals. In the case of those liquid polyol polyesters having high proportions of unsaturated $C_{18}$ or higher fatty acid radicals, at least about half of the fatty acids incorporated into the polyester molecule are typically unsaturated. Preferred unsaturated fatty acids in such liquid polyol polyesters are oleic acid, linoleic acid, and mixtures thereof.

The following are nonlimiting examples of specific liquid polyol polyesters suitable for use in the present invention: sucrose tetraoleate, sucrose pentaoleate, sucrose hexaoleate, sucrose heptaoleate, sucrose octaoleate, sucrose hepta- and octaesters of unsaturated soybean oil fatty acids, canola oil fatty acids, cottonseed oil fatty acids, corn oil fatty acids, peanut oil fatty acids, palm kernel oil fatty acids, or coconut oil fatty acids, glucose tetraoleate, the glucose tetraesters of coconut oil or unsaturated soybean oil fatty acids, the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, and mixtures thereof.

The liquid polyol polyesters suitable for use herein can be prepared by a variety of methods known to those skilled in the art. These methods include: transesterification of the polyol (i.e. sugar or sugar alcohol) with methyl, ethyl or glycerol esters containing the desired acid radicals using a variety of catalysts; acylation of the polyol with an acid chloride; acylation of the polyol with an acid anhydride; and acylation of the polyol with the desired acid, per se. (See, for example, U.S. Pat. Nos. 2,831,854, 3,600,186, 3,963,699, 4,517,360 and 4,518,772, all of which are incorporated by reference. These patents all disclose suitable methods for preparing polyol polyesters.)

III. Solid Polyol Polyester Particles

A second key component of the nondigestible fat compositions of this invention comprises relatively small nondigestible solid particles of certain polyol polyester material that are dispersed in the liquid nondigestible oil to control or prevent passive oil loss. These particles can be in a variety of forms and shapes, including spherulitic, platelet-like, filament-like, or rod-like, or combinations of these various shapes, but are typically spherulitic or platelet-like. The thickness of these particles is typically about 1 micron or less. Thinner particles, however, are preferred from a standpoint of providing more efficient passive oil loss control of the liquid nondigestible oil component of the compositions herein. Accordingly, these particles preferably have a thickness of 0.1 micron or less, more preferably 0.05 micron or less. These particles also have a complete melting point above about 37° C., preferably above about 50° C., more preferably above about 60° C.

These nondigestible particles can generally be dispersed as discrete, unaggregated entities in the liquid nondigestible oil. However, these nondigestible particles can also cluster together to form much larger aggregates which are dispersed in the liquid nondigestible oil. This is particularly true of those nondigestible particles that are platelet-like in form. Aggregates of platelet-like nondigestible particles typically assume a spherulitic shape that is porous in character and thus capable of entrapping significant amounts of liquid nondigestible oil. It is believed that this porous structure and its concomitant ability to entrap large amounts of liquid nondigestible oil is why these aggregated, platelet-like particles, while not as preferred as the particles in unaggregated form, can nevertheless provide very effective and efficient passive oil loss control.

These dispersed nondigestible particles consist essentially of a cocrystallized blend of: (1) a nondigestible solid polyol polyester hardstock; and (2) a crystal modifier. The particular ratio of hardstock to crystal modifier in this cocrystallized blend will depend upon the specific hardstock and/or crystal modifier selected, the specific size of the solid nondigestible particles which are to be dispersed in the oil and the specific passive oil loss control properties desired. In certain cases, such as when the crytal modifier is prepared via acid chloride synthesis, a ratio of hardstock to crystal modifier as high as 99.9:0.1 will be suitable for providing cocrystallized particles having adequate passive oil loss control. Ratios of hardstock to crystal modifier of from about 95:5 to about 20:80 will frequently be suitable for providing cocrystallized particles having adequate passive oil loss control. Preferably, the ratio of hardstock to crystal modifier ranges from about 80:20 to about 20:80, more preferably from about 80:20 to about 40:60, and most preferably from about 70:30 to about 40:60.

A) Hardstock Component of Particle-Forming Blend

The nondigestible solid polyol polyester hardstocks useful in forming the cocrystallized blend used in the present invention are those which provide particles that are solid at temperatures of about 37° C. and higher, and preferably are solid at temperatures of about 50° C. and higher, and most preferably at temperatures of about 60° C. or higher. The polyol polyester hardstock material which ultimately forms the solid oil loss control particles should have a complete melting point as measured by the DSC method described hereinafter in the Analytical Methods section which is sufficiently high such that the particles themselves are solid at the hereinbefore described temperatures. For example, a hardstock material having a complete melting point right at 37° C. may not form particles which are solid at 37° C. when the particles are dispersed in the liquid nondigestible oil. Thus in some cases, the complete melting point of the neat polyol polyester hardstock material may have to be slightly higher than 37° C., e.g. about 40° C. or higher, in order to form particles which are solid at 37° C. when combined with the liquid nondigestible oil.

In the absence of a crystal modifier as hereinafter described, the nondigestible polyol polyester hardstocks useful herein are those materials which normally tend to form spherulitic particles having a diameter of about 3 microns or larger when crystallized in the liquid nondigestible oil. Typically, these spherulitic hardstock particles will range in size from 3 to 32 microns, depending on the level of hardstock present, when crystallized in liquid nondigestible oil in the absence of a crystal modifier. FIGS. 1A, 1B, 1C and 1D are photomicrographs showing a typical sucrose polyester hardstock (sucrose hepta- and octaesters of hydrogenated soybean oil fatty acids) crystallized in liquid nondigestible oil (sucrose hepta- and octaesters of cottonseed oil fatty acids) at 1%, 3%, 6% and 9% solids levels, respectively.

Preferred nondigestible polyol polyester hardstock materials suitable for use herein can be selected from solid sugar polyesters, solid sugar alcohol polyesters and mixtures thereof, and can contain ester groups, e.g., generally 5 to 8 ester groups, which consist essentially of long chain saturated fatty acid radicals. Suitable saturated fatty acid radicals contain at least 14, preferably from 14 to 26, most preferably from 16 to 22, carbon atoms. The long chain saturated fatty acid radicals can be used singly or in mixtures with each other. Straight chain (i.e. normal) fatty acid radicals are typically used for the long chain saturated fatty acid radicals.

Examples of suitable long chain saturated fatty acid radicals useful for forming hardstock polyol fatty acid polyesters include tetradecanoate (myristate), hexadecanoate (palmitate), octadecanoate (stearate), eicosanoate (arachidate), docosanoate (behenate), tetracosanate (lignocerate), and hexacosanoate (cerotate). Mixed fatty acid radicals from completely or substantially completely hydrogenated vegetable oils which contain substantial amounts of the desired long chain saturated fatty acids can be used as sources of fatty acid radicals in preparing the solid polyol polyester hardstock materials useful in the present invention. The mixed fatty acids from such oils should preferably contain at least about 30% (more preferably at least about 50%, most preferably at least about 80%) of the desired long chain saturated fatty acids. Suitable source oils for use in preparing useful polyol polyester hardstocks include completely or substantially completely hydrogenated soybean oil, cottonseed oil, palm oil, peanut oil, corn oil, safflower oil, sunflower oil, sesame oil, low erucic acid rapeseed oil (i.e. canola oil), and high erucic acid rapeseed oil. These oils are typically hydrogenated to an Iodine Value of about 12 or less, and preferably to an Iodine Value of about 8 or less.

Examples of solid polyol polyesters useful as hardstocks in the fat compositions of the present invention include sucrose octabehenate, sucrose octastearate, sucrose octapalmitate, sucrose heptastearate, xylitol pentastearate, galactose pentapalmitate, and the sucrose hepta- and octaesters of soybean oil and high erucic acid rapeseed oil fatty acids that have been hydrogenated to an Iodine Value of about 8 or less.

The solid polyol polyesters useful as hardstocks in the present invention can be made according to prior known methods for preparing polyol polyesters. Since the sucrose polyesters are the preferred solid polyol polyesters for use as hardstocks in the present invention, such preparation will be exemplified primarily by these materials. One such method of preparation is by reacting the acid chlorides or acid anhydrides of the respective acids with sucrose. Another method for preparing these solid polyol polyesters is by the process of reacting the methyl esters of the respective acids with sucrose in the presence of a soap and a basic catalyst such as potassium carbonate. See, for example, Rizzi et al, U.S. Pat. No. 3,963,699, Issued Jun. 15, 1976; Volpenhein, U.S. Pat. No. 4,518,772, Issued May 21, 1985, and Volpenhein, U.S. Pat. No. 4,517,360, Issued May 14, 1985, all of which are incorporated herein by reference.

B) Crystal Modifier Component of Particle-Forming Blend

The second essential component of the cocrystallized blend used to form the solid nondigestible particles in the nondigestible fat compositions herein is a crystal modifier. This crystal modifier can comprise any material which is capable of inducing the solid polyol polyester hardstock materials as hereinbefore described to form smaller particles than such hardstocks would otherwise form if the crystal modifier were not present. Such crystal modifiers will typically be fatty acid ester materials which are solid at temperatures of about 37° C. or higher and which induce the polyol polyester hardstock with which they are cocrystallized to form particles having a thickness of about 1 micron or less. More preferably, such crystal modifiers are solid at temperatures of about 50° C. or higher and tend to induce formation of cocrystallized particles having a thickness of about 0.1 micron or less. Most preferably, such crystal modifiers are solid at temperatures of about 60° C. or higher and tend to induce formation of cocrystallized particles having a thickness of 0.05 micron or less.

Examples of suitable types of crystal modifiers for use herein include diversely esterified polyol polyesters, polyol polyester polymers, polyglycerol esters (PGEs) and other materials such as fatty acid monoglycerides and beeswax. Each of these types of suitable crystal modifiers is described in greater detail as follows:

1) Diversely Esterified Polyol Polyesters

A preferred type of crystal modifier for use in the present invention comprises certain polyol polyesters which have their ester group-forming fatty acid radicals selected so that the polyol backbone does not contain all of a single type of ester group. Generally, such polyol polyester crystal modifiers will contain two basic types of ester groups. These are (a) groups formed from certain long chain saturated fatty acids radicals, and (b) groups formed from acid radicals which are "dissimilar" to the long chain saturated fatty acid radicals. When these "dissimilar" fatty acid and/or other organic acid radicals are esterified onto a polyol that contains or will contain long chain saturated fatty acid radicals, they will introduce diverse esterification into the resulting polyol polyester molecule. This diverse esterification can be due to differences in length of the ester-forming acid radicals (e.g., short chain versus long chain), or other stearic factors, e.g. branched chain versus straight chain, unsaturated chain versus saturated chain, aromatic chain versus aliphatic chain, etc. Polyol polyesters containing these "long chain" and "dissimilar" ester groups are called "diversely esterified polyol polyesters".

a) Long Chain Saturated Fatty Acid Component of the Diversely Esterified Polyol Polyester Crystal Modifiers The ester groups of the diversely esterified nondigestible polyol polyester particles must include those formed from certain long chain saturated fatty acid radicals. Suitable long chain saturated fatty acid radicals comprise those which contain from 20 to 26, most preferably 22, carbon atoms. The long chain saturated fatty acid radicals can be used singly, or in mixtures with each other, in all proportions. In addition, straight chain (i.e. normal) fatty acid radicals are typically used as the long chain saturated fatty acid radicals which form ester groups on the diversely esterified polyol polyester. Examples of suitable long chain saturated fatty acid radicals include eicosanoate (arachidate), docosanoate (behenate), tetracosanoate (lignocerate), and hexacosanoate (cerotate).

b) Dissimilar Ester-Group Forming Component of the Diversely Esterified Polyol Polyester Crystal Modifiers The ester groups of the diversely esterified polyol polyester crystal modifiers must also include those formed from certain dissimilar acid radicals as hereinbefore defined. Such dissimilar radicals can comprise $C_{12}$ or higher unsaturated fatty acid radicals, $C_2$–$C_{12}$ saturated fatty acid radicals or mixtures thereof, or can be of the fatty-fatty acid type, the aromatic ester-forming type, or other types such as ultra long chain or various branched cyclic or substituted acid radicals. These several types of "dissimilar" acid radicals are described in greater detail as follows:

i) Long Chain Unsaturated Radicals

A preferred class of "dissimilar" acid radicals comprises long chain unsaturated fatty acid radicals. Suitable long chain unsaturated fatty acid radicals contain at least 12, preferably from 12 to 26, more preferably from 18 to 22, most preferably 18, carbon atoms.

Examples of suitable long chain unsaturated fatty acid radicals for use in forming diversely esterified polyol polyester crystal modifiers include monunsaturated radicals such as lauroleate, myristoleate, palmitoleate, oleate, elaidate, and erucate, and polyunsaturated radicals such as linoleate, arachidonate, linolenate, eicosapentaenoate, and docosahexaenoate. In terms of oxidative stability, the monounsaturated and diunsaturated fatty acid radicals are preferred.

ii) Short Chain Saturated Radicals

Another preferred class of "dissimilar" acid radicals comprises short chain saturated fatty acid radicals. Suitable short chain saturated fatty acid radicals contain from 2 to 12, preferably from 6 to 12, and most preferably from 8 to 12, carbon atoms. Examples of suitable short chain saturated fatty acid radicals are acetate, butyrate, hexanoate (caproate), octanoate (caprylate), decanoate (caprate), and dodecanoate (laurate).

iii) Fatty-Fatty Acid Dissimilar Ester-Forming Radicals

Another suitable class of dissimilar ester groups comprises those formed by what are designated herein as fatty-fatty acid radicals. As used herein, the term "fatty-fatty acid radical" refers to a fatty acid radical having at least one hydroxyl group that is itself esterified with another fatty or other organic acid.

Examples of fatty acids containing a hydroxyl group that can be esterified with another fatty acid include 12-hydroxy-9-octadecenoic acid (ricinoleic acid), 12-hydroxy-octadecanoic acid, 9-hydroxy-octadecanoic acid, 9-hydroxy-10, 12-octadecadienoic acid, 9-hydroxy-octadecanoic, 9, 10-dihydroxyoctadecanoic acid, 12, 12-dihydroxyeicosanoic acid, and 18-hydroxy-9, 11, 13-octadecatrienoic acid (kamolenic acid). Ricinoleic acid is a preferred hydroxy-fatty acid. Castor oil is a convenient source of ricinoleic acid. Other sources of hydroxy-fatty acids include hydrogenated castor oil, strophanthus seed oils, calendula officinalis seed oils, hydrogenated strophanthus seed oils and hydrogenated calendula officinalis seed oils, cardamine impatiens seed oils, kamala oils, mallotus discolor oils, and mallotus claoxyloides oils.

Hydroxy fatty acids can also be synthetically prepared by oxidative hydroxylation of unsaturated fatty acids using oxidizing agents such as potassium permanganate, osmium tetroxide, and peracids such as peracetic acid. Using this method, 9, 10-dihydroxyoctadecanoic acid can be made from oleic acid, and 9, 10, 12, 13-tetrahydroxy-octadecanoic acid can be made from linoleic acid. Another way to prepare hydroxy fatty acids, such as 10-hydroxy-12-cis-octadecenoic and 10-hydroxy-12 cis, 15-cis-octadecactanoic acids, synthetically is by conversion of fatty acids such as linoleic and linolenic via microorganisms such as Nocardia Cholesteroliim.

Suitable acids for esterification onto the hydroxyl group of the hydroxy-fatty acid radical can be derived from either synthetic or natural, saturated or unsaturated fatty and other organic acids and include positional and geometric isomers. Suitable preferred saturated fatty acids for preparation of the fatty-fatty acid radicals include, for example, acetic, butyric, caproic, caprylic, capric, lauric, myristic, palmitic, stearic, arachidic, behenic, isomyristic, isomargaric, and hydroxystearic. Suitable preferred unsaturated fatty acids for preparation of the fatty-fatty acid radicals include, for example, myristoleic, palmitoleic, ricinoleic, linoleic, oleic, elaidic, linolenic, eleostearic, arachidonic, erucic, and erythrogenic acids. Mixtures of fatty acids derived from soybean oil, palm oil, cottonseed oil, safflower oil, rapeseed oil (high erucic acid), canola (low erucic acid), and corn oil are especially preferred for preparation of the fatty-fatty acid radicals herein. The fatty acids can be used "as is" and/or after hydrogenation, and/or isomerization, and/or purification. For example, rapeseed provides a good source for $C_{22}$ fatty acid. $C_{16}$–$C_{18}$ fatty acids can be provided by tallow, soybean oil, or cottonseed oil. Shorter chain fatty acids can be provided by coconut, palm kernel, or babassu oils. Corn oil, lard, olive oil, palm oil, peanut oil, castor oil, safflower seed oil, sesame seed oil, and sunflower seed oil are examples of other natural oils which can serve as the source of these fatty acids that are esterified onto the hydroxyl group of the hydroxy-fatty acid radical.

Other suitable organic acid radicals for esterification onto the fatty acid radical containing the hydroxyl group to thereby form fatty-fatty acid radicals include aromatic esters such as benzoic or toluic; branched chain radicals such as isobutyric, neoocatanoic or methyl stearic; ultra-long chain saturated or unsaturated fatty acid radicals such as triconsanoic or triconsenoic; cyclic aliphatics such as cyclohexane carboxylic; and polymeric ester-forming radicals such as polyacrylic and dimer fatty acid.

The fatty-fatty acid radicals can be prepared prior to esterification onto the polyol by transesterifying the hydroxy group with the respective fatty acids or fatty acid esters. For example, fatty-fatty radicals of ricinoleic chains can be prepared by esterifying ricinoleic methyl ester with behenic methyl esters. Preferably, an excess of behenic methyl esters is used so that the majority of ricinoleic 12-hydroxy groups are esterified with behenic chains.

A more convenient method of preparing the fatty-fatty radicals is to prepare them in situ before, or preferably during, the esterification of the polyol. For example, one equivalent of sucrose, 1 equivalent of castor oil methyl esters, and 7 equivalents of methyl esters made from hydrogenated and distilled high erucic rapeseed methyl esters could be reacted together, along with a functional amount of emulsifier and basic catalyst. When these ingredients are heated under a vacuum, the esterification of the hydroxy fatty methyl esters (primarily ricinoleic methyl esters) will occur at about the same time as the transesterification of the fatty acid methyl esters with the sucrose. Since the majority of the fatty acid methyl esters are behenic methyl esters in this example, most of the 12-hydroxy groups on the ricinoleic methyl esters will esterify with the behenic methyl esters.

iv) Aromatic Dissimilar Ester-Forming Radicals

Another suitable class of dissimilar ester groups comprises those formed from aromatic radicals. Aromatic radicals can be derived from a wide variety of aromatic compounds including benzoic compounds such as benzoic or toluic acid; amino benzoic compounds such as amino benzoic and aminomethyl benzoic acids; hydroxybenzoic compounds such as hydroxybenzoic, vanillic and salicylic acids; methoxybenzoic compounds such as anisic acid; acetoxyphenylacetic compounds such as acetylmandelic acid; and halobenzoic compounds such as chlorobenzoic, dichlorobenzoic, and fluorobenzoic acids. Other aromatic ester-forming radicals may also be employed such as acetyl benzoic, cumic, phenylbenzoic, and nicotinic; and polycyclic aromatic radicals including fluorene carboxylic, and indole carboxylic. These aromatic-type dissimilar acid radicals can be used singly, or in mixtures with each other, in all proportions.

v) Other Dissimilar Ester-Forming Radicals

Various other ester-forming radicals can also serve as those which form the dissimilar ester groups of the diversely esterified polyol polyester crystal modifiers used herein. Such other acid radicals can be branched alkyl chain, e.g. methyl alkyl radicals such as methyl stearic, isobutyric, and isovaleric; ultra-long chain saturated or unsaturated radicals including tricotanoic and tricontenoic; cyclic aliphatic radicals including cyclobutane carboxylic, cyclopentane carboxylic, cyclohexane carboxylic, cyclohexane acetic, and hydroxycyclic such as ascorbic; polycyclic aliphatic such as abietic; polymer esters such as polyacrylic and dimer fatty acid; and alkyl chain radicals with "functional" groups attached including haloalkyl radicals such as chlorostearic, chlorocaprylic, chloroacetic, bromostearic, bromocaprylic, and bromoacetic; aminoalkyl radicals such as aminocaprylic and aminostearic; phenoylalkyl radicals such as benzoylbutyric; and phenylalkyl radicals such as phenyl acetic. These "other" dissimilar radicals can also be used singly, or in mixtures with each other, in all proportions.

c) Preparation of Diversely Esterified Polyol Polyesters

The diversely esterified polyol polyesters of the type hereinbefore described can be prepared by esterifying the desired polyol with the requisite types of ester-forming radicals. Mixed fatty acid radicals from oils which contain substantial amounts of the desired long chain saturated and/or dissimilar fatty acids can be used as the sources of fatty acid radicals in preparing the solid polyol polyesters used as crystal modifiers in the present invention. The mixed fatty acids from such oils should preferably contain at least about 30% (preferably at least about 50%, and most preferably at least about 80%) of the desired dissimilar and/or long chain saturated fatty acids. For example, palm kernel oil fatty acids can be used instead of a mixture of the respective pure saturated fatty acids having from 8 to 12 carbon atoms. Similarly, rapeseed oil fatty acids or soybean oil fatty acids can be used instead of a mixture of the respective pure monounsaturated and polyunsaturated fatty acids having 12 to 26 carbon atoms, and hardened (i.e., hydrogenated) high erucic rapeseed oil fatty acids can be used in place of a mixture of the respective pure long chain saturated fatty acids having from 20 to 26 carbon atoms. Preferably, the $C_{20}$ or higher saturated fatty acids (or their derivatives, e.g. methyl esters) are concentrated, for example, by distillation.

An example of source oils for preferred diversely esterified polyol polyester crystal modifiers is the combination of high oleic sunflower oil and substantially completely hydrogenated high erucic rapeseed oil. When sucrose is substantially completely esterified with a 1:3 by weight blend of the methyl esters of these two oils, the resulting polyol polyester has a molar ratio of unsaturated $C_{18}$ acid radicals to saturated $C_{20}$ or higher acid radicals of about 1:1, with the saturated $C_{20}$ and $C_{22}$ acid radicals being about 28.6% of the total fatty acid radicals. The higher the proportion of the desired dissimilar and long chain saturated fatty acids in the source oils used, the better the resulting diversely esterified polyol polyesters will function as crystal modifiers.

The diversely esterified solid nondigestible polyol polyester crystal modifiers used herein and prepared from the various sources of acid radicals as outlined hereinbefore will generally contain at least about 15%, preferably at least about 30%, more preferably at least about 50%, most preferably at least about 80%, of the long chain saturated fatty acid radicals along with at least some of the dissimilar acid radicals. In the diversely esterified polyol polyester crystal modifier materials used herein, the molar ratio of dissimilar radicals to long chain saturated fatty acid radicals can range from about 1:15 to about 2:1. Preferably, this molar ratio ranges from about 1:7 to about 5:3, most preferably from about 1:7 to about 3:5.

Specific examples of diversely esterified polyol polyester crystal modifiers useful in the present invention include sucrose tetrabehenate tetracaprylate, sucrose pentabehenate trilaurate, sucrose hexabehenate dicaprylate, and sucrose hexabehenate dilaurate. Other examples include the sorbitol hexaester of palmitoleic and arachidic fatty acid radicals in a 1:2 molar ratio, the raffinose octaester of linoleic and behenic fatty acid radicals in a 1:3 molar ratio, the maltose heptaester of a mixture of sunflower oil and lignoceric fatty acid radicals in a 3:4 molar ratio, the sucrose octaester of oleic and behenic fatty acid radicals in a 2:6 molar ratio, the sucrose octaester of lauric, linoleic and behenic fatty acid radicals in a 1:3:4 molar ratio, and the sucrose hepta- and octaesters of $C_{18}$ mono- and/or di-unsaturated fatty acid radicals and behenic fatty acid radicals in a molar ratio of unsaturated:behenic acid radicals of about 1:7 to 3:5.

The diversely esterified solid polyol polyesters useful herein can be made according to prior known methods for preparing polyol polyesters. Since the sucrose polyesters are the preferred solid polyol polyesters for use in the present invention, such preparation will be exemplified primarily by these materials. One such method of preparation comprises reacting the acid chlorides or acid anhydrides of the desired ester-forming acids or the acids per se with sucrose, preferably using a sequential esterification process. In this sequential esterification process, sucrose is initially partially esterified with the dissimilar acid chlorides, followed by complete or substantially complete esterification of this initial reaction product with the long chain saturated fatty acid chlorides, in that order, or in the reverse order. (See Letton; European Patent 311,154; Published Apr. 12, 1989, herein incorporated by reference.)

Another method for preparing these diversely esterified polyol polyester crystal modifiers is by the process of reacting the methyl esters of the desired ester-forming acids with sucrose in the presence of a fatty acid soap and a basic catalyst such as potassium carbonate. (See, for example, Rizzi et at; U.S. Pat. No. 3,963,699; Issued Jun. 15, 1976; Volpenhein; U.S. Pat. No. 4,518,772; Issued May 21, 1985, and Volpenhein; U.S. Pat. No. 4,517,360; Issued May 14, 1985, all of which patents are incorporated by reference.) When using the methyl ester route to prepare these diversely esterified solid polyol polyesters having mixed dissimilar acid radicals and long chain saturated fatty acid radicals, the octaester of one of the types of acids (e.g., dissimilar acids, or long chain saturated fatty acids) can be prepared first, followed by partially interesterifying this initial reaction product with the methyl ester of the other type of acid. In another preferred way of preparing solid polyol polyester material via a methyl ester process, the methyl esters of the long chain saturated fatty acids are reacted with sucrose in a first stage at about 135° C. to obtain partial esters of sucrose. The methyl esters of the dissimilar acids are then added to the reaction and the temperature is dropped to 90°–120° C., as necessary (and reflux, if required) to achieve the desired degree of esterification.

When using the methyl ester route to prepare these diversely esterified polyol polyester crystal modifiers having mixed dissimilar acid and long chain saturated fatty acid radicals, the dissimilar and long chain Saturated methyl esters are blended in the desired ratio and reacted with sucrose by transesterification to obtain the sucrose esters of mixed dissimilar/long chain saturated fatty acids.

2) Polyol Polyester Polymers

Another preferred type of crystal modifier for use in the invention herein comprises certain polyol polyesters which contain some material in the form of polymerized polyesters, i.e., polyol polyester polymers. Polyol polyester polymers for purposes of this invention are those polyol polyester materials formed by polymerizing a polyol polyester monomer to provide a molecule having at least two separate esterified polyol moieties linked by covalent bonds between ester groups of these different polyol moieties. For example, two sucrose octabehenate moieties could be cross-linked between fatty acids to form a polymer. Repeating units of such polyol polyester polymers can be the same or different such that the generic term "polymer" in this context includes the more specific term "copolymer". The number of repeating monomer (or co-monomer) units which make up such polyol polyester polymers can range from 2 to 20, preferably from 2 to 12. Depending on the method of preparing them, the polyol polyester polymers are frequently oligimers containing from 2 to 4 monomeric units, i.e., are dimers, trimers, or tetramers. The most typical type of polyol polyester polymer for use as a crystal modifier herein is dimer.

Figure 2C:
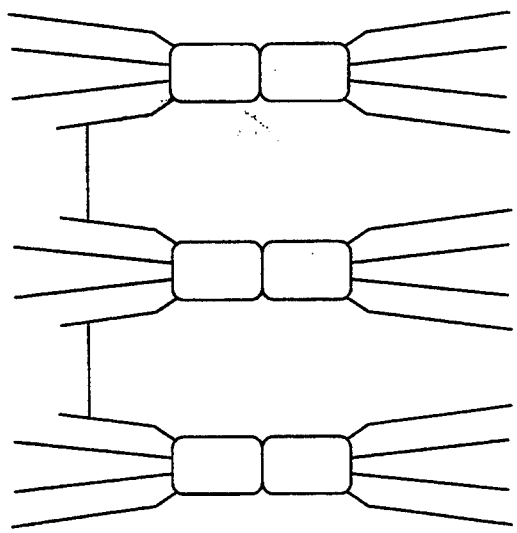
FIGS. 2A through 2C represent depictions of crystal modifiers which are sucrose octaester monomer, dimer and trimer, respectively.
Figure 2B:
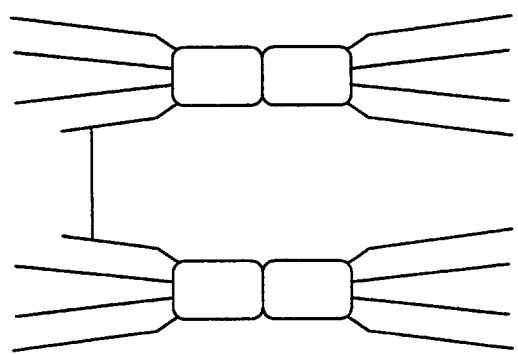
Figure 2A:
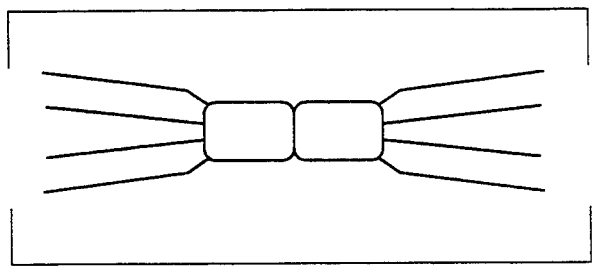
Figure 3:
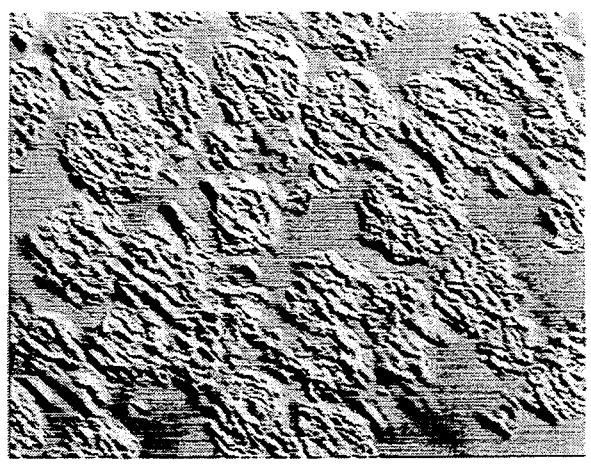
FIGS. 3 through 10 are photomicrographs (magnification of 1,000x) of the several nondigestible fat compositions set forth hereinafter in Table VIII of Example VIII. These compositions comprise a liquid sucrose polyester and a cocrystallized blend of sucrose polyester hardstock and various crystal modifiers.
Figure 4:
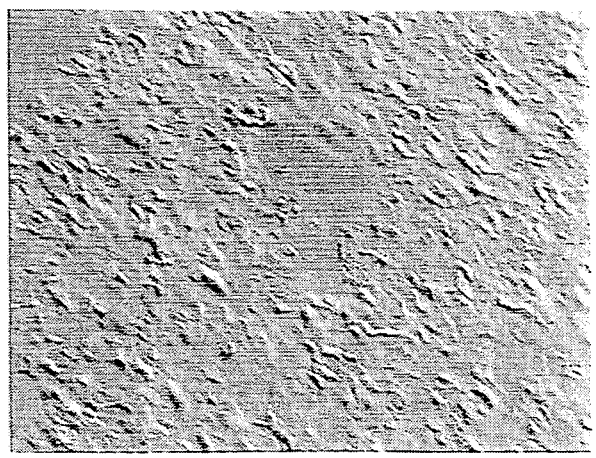
Figure 5:
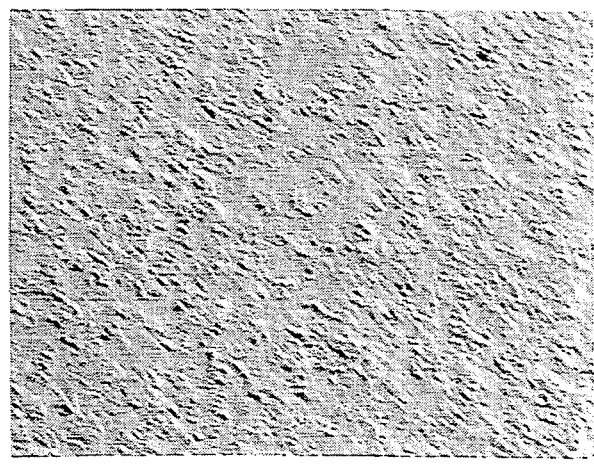
Figure 6:
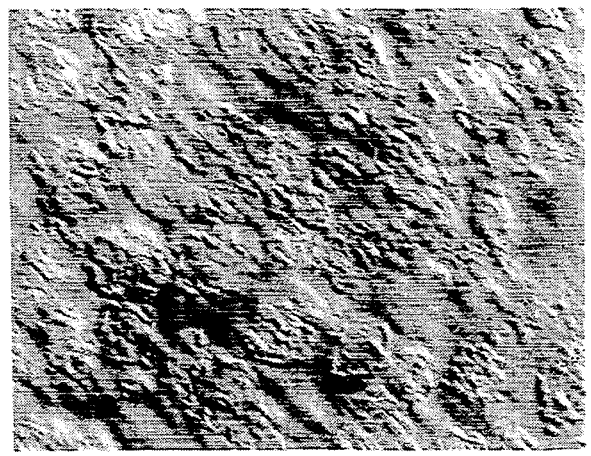
Figure 7:
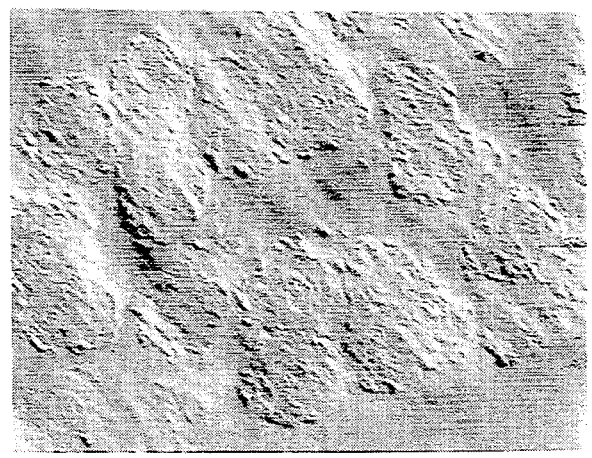
Figure 8:
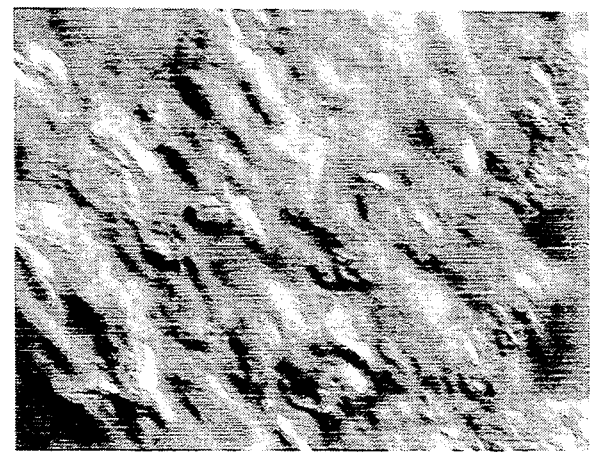
Figure 9:
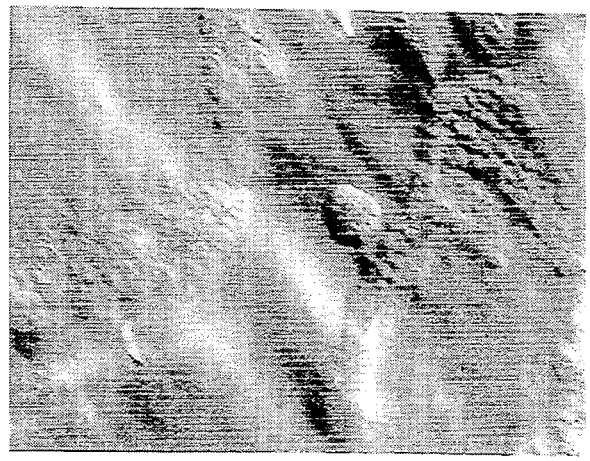
Figure 10:
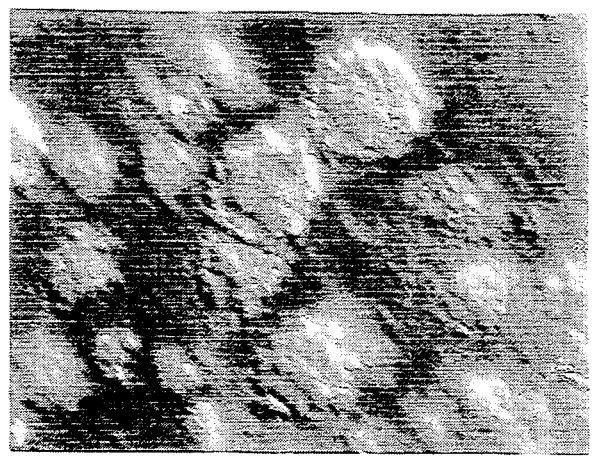

As with the other polyol polyester components of the compositions herein, the most preferred polyol for forming the polyol polyester polymer component comprises sucrose. When sucrose is used, furthermore, it is preferably completely esterified with fatty acid or other ester group-forming acid radicals. Using sucrose as the polyol, completely esterified sucrose polyester monomer, dimer, and trimer are shown schematically in FIGS. 2A, 2B and 2C, respectively. When sucrose is the polyol and the fatty acid ester-forming radicals are selected as hereinafter described in greater detail, the sucrose polyester polymers used as crystal modifiers in the nondigestible fat compositions herein can advantageously have a number average molecular weight of from about 4000 to about 60,000, preferably from about 4000 to about 36,000, more preferably from about 5000 to about 12,000.

The nature of the ester-forming radicals which form the polyol polyester polymer materials is also important in determining the suitability of such polyol polyester polymer materials as crystal modifiers useful in the fat compositions herein. For purposes of this invention, at least about 15%, preferably at least about 45%, more preferably at least about 75%, and most preferably at least about 90% of the hydroxyl groups of the polyol polyester polymer material should be esterified with long chain ($C_{20}$ or higher) saturated fatty acid radicals.

The polymer-containing polyol polyester material useful as a crystal modifier in the fat compositions herein may also comprise unpolymerized polyol polyester monomer material. Such monomers are those which contain only one polyol moiety per molecule, which polyol contains 4 to 8 hydroxyl groups, at least 4 of which are esterified. The ester-forming acid radicals on such polyol polyester monomers are, like the ester groups on the polymer materials, also preferably formed from long chain ($C_{20}$ or higher) saturated fatty acid radicals in the amounts hereinbefore specified for the polymer materials. Further, some of the ester groups of the polyol polyester monomer material may be formed by esterifying the single polyol moiety with polymerized (e.g., dimerized) fatty acid radicals.

Suitable long chain saturated fatty acid radicals for use in preparing the polyol polyester polymers and monomers used as crystal modifiers herein are those which contain at least 20, preferably from 20 to 26, most preferably 22, carbon atoms. The long chain saturated fatty acid radicals can be used singly, or in mixtures with each other, in all proportions. In addition, straight chain (i.e., normal) fatty acid radicals are typical for the long chain saturated fatty acid radicals. Examples of suitable long chain saturated fatty acid radicals are eicosanoate (arachidate), docosanoate (behenate), tetracosanoate (lignocerate), and hexacosanoate (cerotate).

Mixed fatty acid radicals from oils which contain substantial amounts of the desired long chain fatty acids can be used as sources of acid radicals in preparing the polymerized polyol polyester materials useful as crystal modifiers in the present invention. The mixed fatty acids from such source oils should preferably contain at least about 30% (more preferably at least about 50%, most preferably at least about 80%) of the desired long chain saturated fatty acids. For example, hardened (i.e., hydrogenated) high erucic acid rapeseed oil fatty acids can be used in place of a mixture of the respective long chain saturated fatty acids having from 20 to 26 carbon atoms. Preferably, the $C_{20}$ or higher saturated fatty acids (or their derivatives, i.e., methyl esters) are concentrated, for example, by distillation.

Suitable polymerized polyol polyester material which forms the crystal modifiers used in the fat compositions herein will generally comprise from about 1% to about 100% of the polyol polyester polymer component and from 0% to about 99% of the unpolymerized polyol polyester monomer component. Preferably, this crystal modifier polyol polyester material comprises from about 10% to about 100% of the polyol polyester polymer component and from about 0% to about 90% of the monomer component. More preferably such crystal modifier material comprises from about 30% to 100% of the polymer component and from about 0% to about 70% of the monomer component. Most preferably such material comprises from about 50% to 100% of the polymer component and and from 0% to about 50% of the monomer component.

This type of polyol polyester material which is suitable for use as a crystal modifier herein must contain at least some polyol polyester polymer. One way to prepare this material, is by synthesizing monomeric polyol polyester according to known polyol esterification, transesterification and/or interesterification methods and by then polymerizing these monomers. The polymerization step can be initiated and promoted by any of a number of well known methods, including, but not limited to, photochemical reactions and reactions with transition metal ions, heat or free radical initiators such as di-tert-butyl peroxide.

Alternatively, polyol polyester polymers useful as crystal modifiers can be prepared directly by esterifying and/or interesterifying the polyol material with polybasic polymerized fatty acids or their derivatives. Since the sucrose polyesters are preferred materials for use in the present invention, the various types of suitable polyol polyester crystal modifier preparation methods will be exemplified by describing sucrose polyester synthesis. One such synthesis method involves reacting the acid chlorides or acid anhydrides of the desired esterifying polymer acids with sucrose, preferably using a sequential esterification process to produce sucrose containing two different types of ester groups, e.g. polymerized fatty acid groups and unpolymerized fatty acid groups. In this sequential esterification process, sucrose is initially partially esterified with one type of fatty acid chloride, for example, dimer fatty acid chlorides, followed by complete or substantially complete esterification of this initial reaction product with another acid chloride type, e.g., with a long chain unpolymerized saturated fatty acid chloride, in that order, or in reverse order. (See Letton; European Patent No. 311,154; Published Apr. 12, 1989, incorporated herein by reference).

Another method for preparing the polyol polyester polymer crystal modifier material is by the process of reacting the methyl esters of the desired polymer acids with sucrose in the presence of a fatty acid soap and a basic catalyst such as potassium carbonate. (See, for example, Rizzi et al; U.S. Pat. No. 3,963,699; Issued Jun. 15, 1976, Volpenhein; U.S. Pat. No. 4,518,772; Issued May 21, 1985, and Volpenhein; U.S. Pat. No. 4,517,360; Issued May 14, 1985, all of which are incorporated by reference.) When using this methyl ester route to prepare, for example, diversely esterified sucrose polyesters, the octaester of one of the types of acids (e.g., dimer fatty acids, or long chain unpolymerized saturated fatty acids) can be prepared first, followed by partially interesterifying this initial reaction product with the methyl ester of the other type of acid. In another preferred way of preparing polyol polyester crystal modifier material using methyl ester derivatives, the methyl esters of unpolymerized long chain saturated fatty acids can be reacted with sucrose in a first stage at about 135° C. to obtain partial esters of sucrose. The methyl esters of dimer fatty acids or other polybasic polymerized fatty acids can then be added to the reaction and the temperature is dropped to 90°–120° C., as necessary, (and reflux, if required, as with adipic acid methyl esters, for example) to obtain the desired degree of esterification.

When using the foregoing methods for preparing sucrose polyester material containing both unpolymerized and polymerized fatty acid groups, the molar ratio of unpolmerized to polymerized fatty acids in the resulting sucrose polyester material can range from about 1:7 to about 5:3. More preferably this molar ratio can range from about 2:6 to about 4:4.

When using the acid chloride and methyl ester procedures hereinbefore described to esterify polyol with already polymerized fatty acids, a wide variety of prepolymerized fatty acid materials can be used. One such class of suitable polymerized fatty acids comprises long-chain, aliphatic, dibasic acids having from about 28 to about 44 carbon atoms in their molecules. These are generally formed from unsaturated fatty acids having from about 14 to about 22 carbon atoms which can be polymerized. For example, linoleic acid can be polymerized by heating to form linoleic acid dimer as follows:

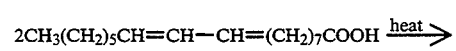

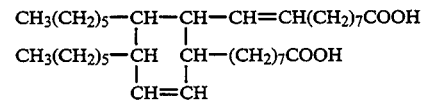

Common examples of polymerizable acids of this type are those containing two or more double bonds (polyunsaturated acids) such as the octadecadienoic acids containing two double bonds, for example, the above-mentioned linoleic acid, and the octadecatrienoic acids containing 3 double bonds, for example, linolenic and eleostearic acids. Other common polymerizable polyunsaturated acids having from about 14 to about 22 carbon which can be used to esterify polyols and thereby form the polyol polyester polymers herein are other octadecatrienoic acids (e.g., licanic acid), octadectetraenoic add (e.g., parinaric acid), eicosadienoic acid, eicostetraenoic acid (e.g., arachidonic acid), 5, 13-docosadienoic acid and clupanodonic acid. Monounsaturated fatty acids, such as oleic, elaidic and erucic acids, can also be used in preparing suitable long chain fatty acid dimers which in turn can then be used to form the polyol polyester polymer crystal modifier particles useful in the present invention.

Mixed fatty acid radicals from source oils which contain substantial amounts of the desired polymerizable polyunsaturated or monounsaturated fatty acids can be used as sources of acid radicals in preparing the polyol polyester polymer materials used to form crystal modifiers useful in the present invention. The mixed fatty acids from such source oils should preferably contain at least about 30% (more preferably at least about 50%, most preferably at least about 80%) of the desired polymerizable polyunsaturated or monounsaturated fatty acids.

Illustrative of natural sources which are rich in linoleic acid are soybean oil, cottonseed oil, peanut oil, corn oil, sesame seed oil, sunflower seed oil, safflower oil, linseed oil and perrilla oil. Oiticica oil is a particularly good source of licanic acid and tung oil contains a high concentration of eleostearic acid. Fish oils, such as herring, manhaden, pilchard, salmon and sardine oil are also suitable sources of polymerizable acids, particularly the higher fatty acids such as arachidonic and clupanodonic acids. Other oils such as tall oil, dehydrated castor oil, olive oil and rapeseed oil also contain significant proportions of suitable unsaturated acids. For example, olive oil is rich in oleic acid and rapeseed oil is rich in erucic acid.

Preferred polybasic polymerized fatty acids and fatty acid derivatives for use in preparing polymer-containing polyol polyester crystal modifiers include dibasic acids produced by dimerization of the fatty acids or fatty acid lower esters derived from polyunsaturated vegetable oils such as soybean oil or cottonseed oil or from animal fats such as tallow.

All of the following types of polybasic polymerized fatty acids may themselves be made by a variety of methods known to those skilled in the art. (See Lutton; U.S. Pat. No. 3,353,967; Issued Nov. 21, 1967, Goebel; U.S. Pat. No. 2,482,761; Issued Sep. 27, 1949, Harrison et al; U.S. Pat. No. 2,731,481; Issued Jan. 17, 1956 and Barrett et al; U.S. Pat. No. 2,793,219; Issued May 21, 1957, all of which are incorporated herein by reference.)

As noted, a mixture of both polymerized and unpolymerized polyol polyester material can be prepared by reacting the polyol with both polymerized and unpolymerized esterifying fatty acids or fatty acid derivatives. In a preferred method for preparing particularly desirable sucrose polyester crystal modifiers comprising sucrose polyester polymers, fractionated or unfractionated high erucic acid rapeseed (HEAR) methyl esters are partially polymerized, hardened and then reacted with sucrose. Another method of making these especially desirable sucrose polyester crystal modifiers is to make liquid sucrose polyester material esterified with fatty acid groups of high erucic acid rapeseed oil by a conventional process, to then partially polymerize the resulting liquid sucrose-polyester material, and to then harden the resulting polymerized material.

3. Polyglycerol Esters

Another preferred type of crystal modifier for use in the invention herein comprises certain polyglycerol esters. Such polyglycerol esters are those which contain at least about 2 glycerol moieties, more preferably from about 3 to about 10 glycerol moieties, even more preferably from about 4 to about 8 glycerol moieties, and most preferably from about 4 to about 6 glycerol moieties. Typically mixtures of polyglycerol esters are employed having an average degree of glycerol polymerization as hereinafter defined in the Analytical Methods section of from about 2 to 10, more preferably from about 3 to 8, most preferably from about 3 to 6. The distribution of the number of glycerol moieties in such polyglycerol ester mixtures may be narrow or broad.

Typical polyglycerol esters useful herein as crystal modifiers have at least about 30% of their hydroxyl groups esterified with fatty acids. Preferably at least about 50% of the hydroxyl groups of the polyglycerol esters are esterified. The percent esterification of the polyglycerol ester materials useful herein can be determined in the manner set forth hereinafter in the Analytical Methods section.

The ester groups which form the polyglycerol ester materials useful herein as crystal modifiers will generally comprise long chain ($C_{16}$–$C_{24}$) fatty acid radicals with at least 40% of these long chain fatty acids being saturated and having at least 18 carbon atoms. Preferably, at least about 50% of these long chain fatty acids are saturated and have at least 18 carbon atoms. More preferably at least about 75% of these long chain fatty acids are saturated have at least 18 carbon atoms. Most preferably at least about 85% of these long chain fatty acids are saturated and have at least 18 carbon atoms.

The fatty acid radicals forming the ester groups on the polyglycerol ester crystal modifiers herein may be saturated or unsaturated. The polyglycerol ester crystal modifiers can, in fact, be further characterized by specifying an Iodine Value which is a measure of the degree of unsaturation of the fatty acids which form the ester groups. The polyglycerol ester crystal modifiers of this invention generally will have an Iodine Value of less than 50, preferably less than about 20, more preferably less than about 10, and most preferably less than about 5.

Mixed fatty acids from source oils (e.g., soybean oil, cottonseed oil, safflower, rapeseed oil, canola, corn oil, sunflower oil, and tallow) which contain the desired fatty acids can be used to form the fatty acid radicals of the ester groups of the polyglycerol ester materials useful herein as crystal modifiers. For example, hardened (i.e., hydrogenated) high erucic rapeseed oil fatty acids can be used instead of pure behenic fatty acid. The fatty acids can be used "as is" and/or after hydrogenation, and/or isomerization, and/or purification. Preferably, the behenic acid (or its derivatives-e.g., methyl esters) are concentrated, for example, by distillation.

The polyglycerol ester materials useful herein as crystal modifiers can be made according to known methods for preparing polyol polyesters. One such method of preparation comprises reacting the acid chlorides or acid anhydrides of the desired ester-forming acids, or the acids per se, with polyglycerol. This can be accomplished using a sequential esterification process or a process in which all the fatty acids are mixed together and added at once. See Letton; European Patent 311,154; published Apr. 12, 1989 (herein incorporated by reference).

Another method for preparing these useful polyglycerol ester crystal modifiers is by a process which comprises reacting the methyl esters of the respective desired acids with polyglycerol in the presence of a fatty acid soap and a basic catalyst such as potassium carbonate. See, for example, Rizzi et al; U.S. Pat. No. 3,963,699; issued Jun. 15, 1976; Volpenhein; U.S. Pat. No. 4,518,772; Issued May 21, 1985; and Volpenhein; U.S. Pat. No. 4,517,360; Issued May 14, 1985, all of which relate to polyol polyester synthesis and which are incorporated by reference.

4. Other Crystal Modifier Types

Other fatty acid-based organic materials may also be useful as crystal modifiers in forming the solid nondigestible oil loss control particles which are part of the nondigestible fat compositions herein. Such materials include, for example, monoglycerides, naturally occurring waxes with long chain alkyl or ester groups, paraffinic hydrocarbon microcrystalline waxes and long chain alcohols.

Monoglycerides are glycerol esters of fatty acids in which only one acid group is attached to the glycerol moiety. Preferred for use herein are monoglycerides of $C_{18}$ and higher saturated fatty acids. Monobehenin is particularly preferred.

A preferred naturally occurring wax material is beeswax. Beeswax is wax from the honeycomb of the bee. Beeswax consists largely of myricyl palmitate, cerotic acid and esters and some high carbon paraffins.

IV. Preparation of Nondigestible Fat Compositions Which Exhibit Minimal Passive Oil Loss To prepare the nondigestible fat compositions herein, a mixture comprising the liquid nondigestible oil and a cocrystallizable blend of the polyol polyester hardstock and crystal modifier in an amount of the blend sufficient to control or prevent passive oil loss is formed. What constitutes "an amount sufficient to control or prevent passive oil loss" with regard to the cocrystallizable blend depends upon the specific polyol polyester hardstock and crystal modifier selected, the degree of passive oil loss control benefit desired, and the amount of waxiness impression which can be tolerated for the particular end product use of the nondigestible fat.

Typically, the oil/blend mixture comprises from about 60% to about 99% liquid nondigestible oil, and from about 1% to about 40% of the cocrystallizable blend. Preferably, this mixture comprises from about 80% to about 99% liquid nondigestible oil and from about 1% to about 20% of the cocrystallized blend, more preferably from about 85% to about 99% liquid nondigestible oil and from about 1% to about 15% of the cocrystallizable blend, even more preferably from about 90% to about 99% liquid nondigestible oil and from about 1% to about 10% of the cocrystallizable blend, and most preferably from about 95% to about 99% liquid nondigestible oil and from about 1% to about 5% of the cocrystallizable blend. The use of higher levels of liquid nondigestible oil (i.e. lower levels of the cocrystallizable blend) can be desirable from the standpoint of reducing the waxiness impression of the resulting nondigestible fat. However, higher levels of the cocrystallizable blend (i.e. lower levels of liquid nondigestible oil) are desirable from the standpoint of controlling or preventing the passive oil loss associated with the ingestion of such liquid nondigestible oils.

The mixture of liquid nondigestible oil and the cocrystallizable blend of polyol polyester hardstock and crystal modifier is heated to a temperature which is sufficient to completely melt all of the solid components present in the mixture. This temperature will depend on the specific hardstock and crystal modifier present in the blend. Typically, this melted mixture can be obtained by heating the combination of components to a temperature which is at least about 20° C. higher than the melting point of the highest melting component. The crystal modifier may or may not have a melting point higher than that of the hardstock polyol polyester. Once melted, this mixture is generally stirred to ensure its homogeneity of composition.

The melted mixture so formed can then be crystallized in a manner such that the cocrystallizable blend forms, in the liquid nondigestible oil, dispersed nondigestible particles having the thickness and complete melting point characteristics hereinbefore described. The particular conditions for crystallizing this melted mixture to provide these dispersed nondigestible particles will depend upon the liquid nondigestible oil used, the particular polyol polyester hardstock and crystal modifier selected for use in the cocrystallizable blend, and whether the polyol polyester hardstock or the crystal modifier has the higher melting point. In the typical case where the crystal modifier has a higher melting point than that of the polyol polyester hardstock, the melted mixture can be cooled to any temperature that is below the crystallization temperature of the polyol polyester hardstock. For example, if the crystal modifier has a melting point of about 70° C. while the polyol polyester hardstock has a melting point of about 60° C., cooling the melted mixture to a temperature of about 40° C., or less, preferably about 25° C. or less, more preferably about 10° C. or less, and most preferably about 0° C. or less, would be appropriate.

In the less typical situation of where the melting point of the polyol polyester hardstock is higher than that of the crystal modifier, the melted mixture should be cooled such that the crystal modifier cocrystallizes with the hardstock. If the crystal modifier melts at a significantly lower temperature than that of the polyol polyester hardstock, the melted mixture needs to be cooled to a relatively low temperature so that cocrystallization can occur. For example, if the melting point of the crystal modifier is about 10° C. and that of the polyol polyester hardstock is about 60° C., the melted mixture typically should be cooled to about 0° C. or less to cause appropriate cocrystallization.

The size of the cocrystallized particles formed in the fat compositions herein will be dependent upon the rate at which the heated combination of oil and dissolved solid is cooled. As used herein, cooling rate is defined as the temperature differential between (a) the heated oil/dissolved solid combination and (b) the cooled crystallized liquid/solid particle combination, divided by the time taken to create this temperature differential. Generally the greater the cooling rate employed in forming the fat compositions herein, the smaller will be the cocrystallized particles of solid polyol polyester material dispersed in such compositions. Desirable cooling rates for use in forming the fat compositions herein are typically greater than 0.6° C./min. (1° F./min.), preferably greater than 2.8° C./min. (5° F./min.), more preferably greater than 5.6° C./min. (10° F./min.), and most preferably greater than 27.8° C./min. (50° F./min.). When the nondigestible fat compositions herein are to be formed in situ., for example, within a food product of which they form a part, then the type and concentration of the fat composition components should be selected so that the cooling profile experienced by the food product will result in formulation of the desired amount and size of the solid cocrystallized polyol polyester particles within the food product.

The formation of relatively small nondigestible particles from the hardstock/crystal modifier blends herein is surprising since the polyol polyester hardstock normally tends to form much larger spherulitic particles in the liquid nondigestible oil. This normal tendency is believed to be due to the "symmetrical" nature of the polyol polyester hardstock molecules. The symmetrical nature of these molecules causes them to pack closely together and grow in an unrestrained, three dimensional fashion as large spherulitic particles.

By contrast, suitable crystal modifiers according to the present invention tend to have "asymmetrical" or irregular molecular structures. It is believed that the asymmetrical structure of these crystal modifier molecules interfere with the normal packing tendency of the symmetrical polyol polyester hardstock molecules during cocrystallization in the liquid nondigestible oil. This interference blocks the usual unrestrained three dimensional growth of the symmetrical hardstock molecules and thus induces restrained three dimensional growth or otherwise induces growth in, at most two dimensions, e.g., the formation of relatively thin platelet-like particles.

The formation of thin nondigestible particles according to the present invention provides especially efficient passive oil loss control for the resulting fat composition. Such efficiency permits a reduction in solids content of the nondigestible fat to relatively low levels (e.g., to from about 1% to about 15%). This reduction in solids levels required for passive oil loss control, together with the minimal/no change in solids between typical room and body temperatures, leads to nondigestible fats having a less waxy tasting impression.

Both the liquid nondigestible oil and the solid nondigestible cocrystallized polyol polyester components, as well as their respective concentrations, are selected in order to provide nondigestible fat compositions having a certain set of physical characteristics. In particular, the nondigestible fats of the present invention should exhibit a relatively flat Solid Fat Content (SFC) profile slope across the temperature range of from room temperature to body temperature, i.e., from 70° F. (21° C.) to 98.6° F. (37° C.). The SFC profile slope between these two temperatures should be from 0 to about $-0.75\%$ solids/°F., preferably from 0 to $-0.5\%$ solids/°F., more preferably from 0 to about $-0.3\%$ solids/°F., and most preferably from 0 to about $-0.1\%$ solids/°F. The method for determining SFC profile slope of the fat compositions herein is described hereinafter in the Analytical Methods section.

V. Food Products With Nondigestible Fat Compositions

The nondigestible fat compositions of the present invention can be used in various edible fat-containing products including foods, beverages and pharmaceuticals, either alone or in combination with other materials such as digestible fats and oils. In particular, the nondigestible fats of the present invention can be optionally formulated with a digestible triglyceride fat or oil. Generally, these formulations can comprise from about 10 to 100% nondigestible fat and from 0 to about 90% digestible triglyceride fat or oil. Preferably, these formulations comprise from 35 to 100%, more preferably from about 50 to about 100% and most preferably from about 75 to about 100% nondigestible fat, and from 0 to about 65%, more preferably from 0 to about 50%, and most preferably from 0 to about 25%, digestible triglyceride fat or oil. Because of the potential caloric impact of these triglyceride fats or oils, it is desirable to minimize the level at which they are combined with the nondigestible fats of the present invention.

As used herein, the term "triglyceride oil" refers to those triglyceride compositions which are fluid or liquid above about 25° C. Although not a requirement, the triglyceride oils useful in the present invention can include those which are fluid or liquid below 25° C. These triglyceride oils consist primarily of triglyceride materials, but can also include residual levels of other components such as mono- and diglycerides. To remain fluid or liquid at temperatures below 25° C., the triglyceride oil contains a minimal amount of glycerides having melting points higher than about 25° C. so as to limit the solids increase when the triglyceride oil is cooled. It is desirable that the triglyceride oil be chemically stable and resistant to oxidation.

Suitable triglyceride oils can be derived from naturally occurring liquid vegetable oils such as cottonseed oil, soybean oil, safflower oil, corn oil, olive oil, coconut oil, palm kernel oil, peanut oil, rapeseed oil, canola oil (i.e., rapeseed oil low in erucic acid), sesame seed oil, sunflower seed oil, and mixtures thereof. Also suitable are liquid oil fractions obtained from palm oil, lard and tallow by, for example, graining or directed interesterification, followed by separation of the oils. Oils predominating in glycerides of unsaturated acids may require partial or touch hydrogenation to maintain flavor, but care should be taken not to greatly increase the amount of glycerides melting above 25° C. When oils are selected which have a larger amount of solids melting between 25° and 40° C. than are desirable, it can be necessary to separate out the solids. For example, refined and slightly hydrogenated, and filtered soybean oil is suitable, as well as refined cottonseed oil.

As used herein, the term "triglyceride fat" refers to those triglyceride compositions which are solid or plastic above about 25° C. These solid or plastic fats can be derived from plants or animals or can be edible synthetic fats or oils. For example, animal fats such as lard, tallow, oleo oil, oleo stock, oleo stearin and the like which are solid at room temperature can be utilized. Also, triglyceride oils, e.g. unsaturated vegetable oils, can be converted into plastic fats by partial hydrogenation of the unsaturated double bonds of fatty acid constituents of the oil followed by conventional chilling and crystallization techniques or by proper mixture with sufficient triglycerides which are solid at room temperature to form a rigid interlocking crystalline structure which interferes with the free-flowing properties of the liquid oil. See Purves et at; U.S. Pat. No. 3,355,302; Issued Nov. 28, 1967, and Darragh et al; U.S. Pat. No. 3,867,556; Issued Feb. 18, 1975 (both incorporated herein by reference), for further examples of solid or plastic fats. Because the solid or plastic fats add an appreciable level of solids, their inclusion can cause adverse effects on the organoleptic properties, in particular waxiness, of the edible fat-containing products of the present invention.

Triglyceride fats and oils useful in the nondigestible fats of the present invention can include certain triglycerides in which one, two or three of the OH groups of the glycerol molecule have been substituted with acetyl, propionyl, butyryl, caproyl, caprylyl, or capryl radicals, and the remaining OH groups of the glycerol molecule (if any) have been substituted with acyl radicals of saturated or unsaturated fatty acids having from 12 to 24 carbon atoms. The nondigestible fat compositions herein can also be used in combination with reduced calorie medium chain and mixed medium/long chain triglycerides such as are disclosed in Ehrman et al; U.S. Pat. No. 4,888,196; Issued Dec. 19, 1989 and Seiden; European Patent Application 322,027; Published Jun. 28, 1989, both incorporated herein by reference.

The nondigestible fat composition of the present invention can be used in or as shortening and oil products. The shortening and oil products can be used in frying applications such as preparation of french fried potatoes, potato chips from potato slices or fabricated potato pieces, potato sticks, corn chips, tortilla chips, donuts, chicken, fish, and fried pies (e.g. turnovers). The shortening and oil products can also be used in preparing baked goods in any form, such as mixes, shelf-stable baked goods, and frozen baked goods, including, but not limited to, cakes, granola bars, brownies, muffins, bar cookies, wafers, biscuits, pastries, pies, pie crusts, and cookies, including sandwich cookies, chocolate chip cookies, particularly storage stable dual-texture cookies as disclosed in Hong et al; U.S. Pat. No. 4,455,333; Issued Jun. 19, 1984. These baked goods can contain fruit, cream, or other fillings. Other baked good uses include breads and rolls, crackers, pretzels, pancakes, waffles, ice cream cones and cups, yeast-raised bake goods, pizza and pizza crust, and baked farinaceous snack products and other baked salted snacks.

Other edible fat-containing products which contain the nondigestible fat compositions of the present invention include ice cream, frozen desserts, cheese, cheese spreads, meats, meat analogs, chocolate confections, salad dressings, mayonnaise, margarine, spreads, sour cream, yogurt, coffee creamer, peanut butter, extruded snacks such as corn curls, corn puffs, pellet snacks, half products and other extruded snacks based on corn or other cereal grains such as wheat, rice and the like, roasted nuts and beverages such as milkshakes.

Edible fat-containing products which contain the nondigestible fat compositions of this invention can include noncaloric or reduced calorie sweeteners alone or in combination with bulking agents. These noncaloric or reduced calorie sweeteners include, but are not limited to, aspartame, saccharin, alitame, thaumatin, dihydrochalcones, acesulfame, and cyclamates.

Bulking or bodying agents which can be useful in edible fat-containing products according to the present invention include partially or wholly nondigestible carbohydrates, for example, polydextrose and cellulose or cellulose derivatives, such as D,L-sugars, carboxymethylcellulose, carboxyethylcellulose, hydroxypropylcellulose, methylcellulose, hydroxypropyl methylcellulose, and microcrystalline cellulose. Other suitable bulking agents include gums (hydrocolloids), starches, dextrins, fermented whey, tofu, maltodextrins, polyols, including sugar alcohols, e.g., sorbitol and mannitol, and carbohydrates, e.g., lactose.

The edible fat-containing products containing the nondigestible fat compositions herein can also include dietary fibers. By "dietary fiber" is meant complex carbohydrates resistant to digestion by mammalian enzymes, such as the carbohydrates found in plant cell walls and seaweed, and those produced by microbial fermentation. Examples of these complex carbohydrates are brans, celluloses, hemicelluloses, pectins, gums and mucilages, seaweed extract, and biosynthetic gums. Sources of the cellulosic fiber include vegetables, fruits, seeds, cereals, and man-made fibers (for example, by bacterial synthesis). Commercial fibers such as purified plant cellulose, or cellulose flour, can also be used. Naturally occurring fibers can be used, such as psyllium and fibers from whole citrus peel, citrus albedo, sugar beets, citrus pulp and vesicle solids, apples, apricots, and watermelon finds.

These dietary fibers can be in a crude or purified form. The dietary fiber used can be of a single type (e.g., cellulose), a composite dietary fiber (e.g., citrus albedo fiber containing cellulose and pectin), or some combination of fibers (e.g., cellulose and a gum). The fibers can be processed by methods known to the art.

The nondigestible fat compositions of the present invention can also be fortified with vitamins and minerals, particularly the fat-soluble vitamins. The fat-soluble vitamins include vitamin A, vitamin D, and vitamin E and their precursors. See Mattson; U.S. Pat. No. 4,034,083; Issued Jul. 5, 1977 (herein incorporated by reference) which discloses fat-soluble vitamins useful in fortifying polyol fatty acid polyester.

Various other ingredients typically present in fat products can also be included in the nondigestible fat compositions of the present invention. These other ingredients include stabilizers to help protect against oxidative deterioration at high temperatures. Silicone oils, particularly methyl and ethyl silicone oils, are useful for this purpose. Methyl silicones have also proven effective in reducing the rate of polymerization during frying. Other additives typically included in fat products such as minor amounts of optional flavorings, emulsifiers, anti-spattering agents, anti-sticking agents, antioxidants or the like can also be present.

VI. Alternate Utility for Cocrystallized Polyol Polyester Particles

It has been found that the cocrystallized polyol polyester particles useful as oil loss control agents in the nondigestible fat compositions herein are also effective for use as thickening agents in conventional digestible triglyceride oils and oil-containing products. Accordingly, these cocrystallized polyol polyester particles can be used as "thickening agents" or "hardstocks" by blending them in amounts of about 2% to about 20% (preferably 2–15%, most preferably from about 2% to about 10%) with liquid digestible oils in the formulation of cooking and salad oils or semi-solid food products such as shortenings, as well as other food products which contain a combination of fat and non-fat ingredients, e.g., margarines, mayonnaise, frozen dairy desserts and the like. The oils for these compositions can comprise conventional digestible triglyceride oils such as cottonseed, corn, canola or soybean, or medium or medium and long chain triglycerides.

VII. Analytical Methods

A number of parameters used to characterize elements of the present invention are to be quantified by particular experimental analytical procedures. Each of these procedures is described in detail as follows:

A) Fatty Acid Composition of Polyol Polyesters

The fatty acid composition (FAC) of polyol polyesters useful herein can be determined by gas chromatography, using a Hewlett-Packard Model S712A gas chromatograph equipped with a flame ionization detector and a Hewlett-Packard Mode 17671A automatic sampler. The chromatographic method used is described in Official Methods and Recommended Practices of the American Oil Chemists Society, 4th Ed., 1989, Procedures 1-Ce62 (incorporated herein by reference).

B) Ester Distribution of Sucrose Polyesters

The relative distribution of the individual octa-, hepta-, hexa- and penta- esters, as well as collectively the tetra- through mono- esters, of the preferred sucrose polyesters useful herein can be determined using normal-phase high performance liquid chromatography (HPLC). A silica gel-packed column is used in this method to separate the polyester sample into the respective ester groupings noted above. Hexane and methyl-t-butyl ether are used as the mobile phase solvents. The ester groupings are quantitated using a mass detector (i.e. an evaporative light-scattering detector). The detector response is measured and then normalized to 100%. The individual ester groups are expressed as a relative percentage.

C) Slope of Solid Fat Content (SFC) Profile of Nondigestible Fat, Measured in °F.

Before determining the SFC values, a sample of the nondigestible fat is heated to a temperature of 140° F. (60° C.) or higher for at least 30 minutes or until the sample is completely melted. The melted sample is then tempered as follows: at 80° F. (26.7° C.) for 15 minutes; at 32° F. (0° C.) for 15 minutes; at 80° F. (26.7° C.) for 30 minutes; at 32° F. (0° C.) for 15 minutes. After tempering, the SFC values of the sample at temperatures of 50° F. (10° C.), 70° F. (21.1° C.), 80° F. (26.7° C.), 92° F. (33.3° C.), and 98.6° F. (37° C.) are determined by pulsed nuclear magnetic resonance (PNMR) after equilibration for 30 minutes at each temperature. The slope of the SFC profile is calculated by subtracting the SFC value at 70° F. (21.1° C.) from the SFC value at 98.6° F. (37° C.) and then dividing by 28.6. The method for determining SFC values by PNMR is described in *J. Amer. Oil Chem. Soc.*, Vol. 55 (1978), pp. 328–31 (herein incorporated by reference, and A.O.C.S. Official Method Cd. 16–81, *Official Methods and Recommended Practices of The American Oil Chemists Society*, 4th. Ed., 1989, (herein incorporated by reference).

D) Complete Melting Point of Polyol Polyesters by Differential Scanning Calorimetry (DSC)

The complete melting point of the polyol polyester materials or polyol polyester-containing particles used in this invention can be determined by DSC as follows:

Equipment:
Perkin-Elmer 7 Series Thermal Analysis System, Model DSC7, manufactured by Perkin-Elmer, Norwalk, Conn.

Procedure:
1. Sample of polyol polyester or polyol polyester-containing blend is heated to at least 10° C. above the temperature at which all visible solids are melted and mixed thoroughly.
2. 10±2 mg of sample is weighed into sample pan.
3. A scan is performed from about 10° C. above the temperature at which all visible solids are melted to −60° C. at 5° C. per minute.
4. The temperature of the sample is maintained at −60° C. for 3 minutes and scanned from −60° C. to the original starting temperature at 5° C. per minute (i.e., from about 10° C. above the temperature at which all visible solids are melted).
5. The complete melt point is the temperature at the intersection of the base line (i.e. specific heat line) with the line tangent to the trailing edge of the last (highest temperature) endothermic peak.

E) Thickness of Cocrystallized Polyol Polyester Particles (Light Microscopy)

The thickness of the cocrystallized polyol polyester particles formed in the nondigestible fat compositions herein may be estimated at room temperature with a Nikon Microphot video-enhanced light microscope (VELM) using Hoffman Modulation Contrast (HMC) optics according to the following method:

1. A small portion (i.e., 1–10 mg) of the nondigestible fat sample with the cocrystallized polyol polyester particles dispersed therein is placed on a microscope slide and covered. The slide is placed under the microscope.
2. The sample is examined using a HMC 100X oil objective as the standard lens in conjunction with a 10X eyepiece lens.
3. A microscope-mounted video camera and associated controller are used for video enhancement to facilitate differentiation between the sample and the background.
4. The thickness of the cocrystallized polyol polyester particles is measured in um.

This method permits differentiation of particles having thicknesses just within the resolution of the VELM (approximately 0.2–0.5 um). Particle thickness of particles having smaller dimensions can be determined by the Freeze Fracture Method described hereinafter.

(Note: No special sample preparation is required, other than obtaining a representative sample. The samples should be melted and cooled ambiently.)

Reference: Robert Hoffman, "The Modulation Contrast Microscope: Principles and Performances", *Journal of Microscopy*, Vol. 110, Pt 3, Aug. 1977, pp. 205–222.

F) Thickness of Cocrystallized Polyol Polyester Particles-Freeze Fracture Transmission Electron Microscopy The three-dimensional topography of cocrystallized polyol polyester particles can be determined, and their size determined by a freeze-fracture transmission electron microscopy method.

This freeze-fracture method is carded out as follows:
1. The outside cavity of a freezing container is filled with liquid $N_2$ and the inner dewar of the freezing container is filled with liquid ethane (normal melting temperature of −172° C.). The ethane is allowed to freeze.
2. A small amount (1–2 ul) of the nondigestible fat sample with the solid cocrystallized polyol polyester particles dispersed therein is placed in the well of a gold-plated Balzers specimen holder. (Note: for very fluid samples, 1–2 ul of sample is placed on a gold planchet (Balzers) and another planchet is placed on top of the first to form a sandwich.)
3. Most of the frozen ethane in the dewar is melted by inserting a metal heat sink, e.g., tweezers, into the dewar.
4. Immediately after melting the ethane, the specimen holder containing the nondigestible fat sample is picked up using a pair of tweezers and rapidly plunged into the liquid ethane.

5. After a few seconds, the specimen holder is removed from the ethane, quickly touched to the tip of a camel's hair brush to remove excess-ethane, and immediately immersed in the liquid $N_2$ to keep the sample cold.
6. The sample is transferred under liquid $N_2$ to a JEOL JFD-9000C sample holder and then transferred into the chamber of a JEOL JFD-9000C freeze-fracture unit. The temperature of the unit should be about $-175°$ C. Vacuum should be at least $8 \times 10^{-7}$ torr.
7. A knife is cooled to a temperature of about $-165°$ C.
8. The sample is fractured in the JEOL chamber using the pre-cooled knife.
9. Platinum-carbon is deposited onto the fractured sample at a 45° angle for 4.5 seconds, followed by carbon deposition at a 90° angle for 25 seconds to form a replica of the fractured sample. The high voltage is 2500 V and the current is 70 mA.
10. The samples are removed from the freeze fracture unit and cleaned using 3 washes of chloroform.
11. The replica is picked up on a 300 mesh copper EM grid and examined in a transmission electron microscope.
12. Images are recorded on negative film and positive prints are made from the negatives.
13. The thickness of the cocrystallized polyol polyester particles is measured in nm.

References:

Rash, J. E. and Hudson, C. S., *Freeze Fracture: Methods, Artifacts, and Interpretations,* New Haven Press, New York, 1979.

Stolinski and Breathnach, *Freeze Fracture Replication of Biological Tissues.,* Academic Press, London, 1975.

Steinbrecht and Zierold, *Cryotechniques in Biological Electron Microscopy, Springer-Verlag,* Berlin, 1987.

G) Saponification Value of Polyol Polyester Material

A polyol polyester sample can be saponified with refluxing alcoholic KOH according to the procedure described in *Official Methods and Recommended Practices of the American Oil Chemists Society,* 4th Ed., 1989, Procedure Cd 3-25. The resulting fatty acid soaps are titrated with standardized HCl to a phenolphthalein endpoint. A blank (no sample added) is also run through the procedure and titrated.

The saponification Value is then calculated according to the following equation:

$$SV = ((B-S) \times N \times 56.1)/W$$

Where B=vol. (mls) HCl required to titrate blank
S=vol. (mls) HCl required to titrate sample
N=normality of the HCl
W=sample weight in grams H) Acid Value of Polyol Polyester Material To determine Acid Value, a polyol polyester sample can be titrated with standardized KOH to a phenolphthalein endpoint. The procedure is described in *Official Methods and Recommended Practices of the American Oil Chemists Society,* 4th Ed., 1989, Procedure Cd 3a-63. A blank (no sample added) is titrated also.

The Acid Value is then calculated according to the following equation:

$$AV = ((A-B) \times N \times 56.1)/W$$

Where A=volume in mls of KOH required to titrate sample
B=volume in mls of KOH required to titrate blank
N=normality of the KOH
W=sample weight in grams I) Hydroxyl Value of Polyol Polyester Material The free hydroxyl groups of a polyol polyester sample can be quantatively acetylated with acetic anhydride in pyridine. After acetylation, residual acetic anhydride is hydrolyzed with excess water and the acetic acid remaining is titrated with standardized ethanolic KOH to a phenolphthalein endpoint. A blank (no sample added) is run through the procedure and titrated also. The procedure is described in *Official Methods and Recommended Practices of the American Oil Chemists Society,* 4th Ed., 1989, Procedure Cd 13-60.

The hydroxyl value is then calculated according to the following equation:

$$HV = (((B-S) \times N \times 56.1)/W) + AV$$

where B=volume in mls of KOH required to titrate the blank
S=volume in mls of KOH required to titrate the sample
N=normality of the KOH
AV=acid value of the sample (hereinbefore described)

J) Polymer Content of Polymer-Containing Polyol Polyester Crystal Modifiers

The relative amounts of monomer and total polymer material (e.g., sucrose polyester dimer, trimer, tetramer, etc.) in polymer-containing solid polyol polyester crystal modifier material can be determined using size exclusion chromatography. This method uses a Hewlett-Packard HP-1090 liquid chromatography system (LC) in combination with a Polymer Laboratories 60 cm×7.5 mm, 500A porosity 5 um column. The LC is set up to mn under the following conditions:

| | |
|---|---|
| Injection Volume | 20 uL/min |
| Flow Rate | 1.0 uL/min |
| Mobile Phase | Filtered & Degassed Tetrahydro-furan (THF) |
| Detector Attenuation | 32 X |
| Detector Temperature | 40° C. |
| Chart Speed | 5.0 mm/min |

A polymer-containing polyol polyester crystal modifier sample (0.75 grams) is dissolved in 25 cc of THF, and then 20 microliters of this solution is injected into the LC system. The column separates the sample into monomer and polymer. The fractions are analyzed by a refractive index detector (Erma Optical Works ERC-7512). The detector response is then measured by an integrator. Relative peak areas eluting earlier than polyol polyester monomer are manually summed to report % polymer in the sample.

The various polymer fractions (e.g., monomer, dimer, trimer, tetramer, etc.) are resolved into individual peaks on a strip chart. The monomer peak is identified by comparison with a previously run monomer standard. The elution order (increasing time) is tetramer and higher, trimer, dimer and monomer. The instrument calculates the area under each peak. The weight percent of an individual polymeric species is the area under the species peak, divided by the sum of the areas under all the peaks.

K) Polyglycerol Ester (PGE) Analyses

1 Average Degree of Glycerol Polymerization

The "average degree of glycerol polymerization" (n-bar) is a molar quantity which describes the the average number of glycerol moieties in the polyglycerol ester species comprising a polyglycerol ester mixture. The average degree of glycerol polymerization is calculated from an experimentally determined distribution of the weight percentages of the individual polyglycerol ester species which make up a given mixture of polyglycerol esters.

The distribution of polyglycerol ester species in a polyglycerol ester sample can be determined as follows: the polyglycerol ester sample is transesterified with sodium methoxide in refluxing methanol. The sodium methoxide is removed from the resulting solution by treatment with an anion exchange resin. The methanolic solution of polyglycerols and resulting methyl esters is extracted with hexane to remove the methyl esters. Finally, the methanol is evaporated, leaving the mixture of unesterified polyglycerols. The polyglycerols thus obtained are derivatized with a 5/1 (by volume) mixture of trimethylsilyl imadazole and bis(trimethylsilyl)trifluoroacetamide in pyridine to form trimethylsilyl ethers. The sample is analyzed by GC using a short (18 inches by ⅛ inch ID), packed column (3% JXP, on 100/120 mesh Gas Chrom Q), on column injection and flame ionization detection. The GC method is essentially that used for the separation of intact mixtures of mono-, di-, and triglycerides described in *JAOCS*, 58, (1981) pages 215–227.

The average degree of glycerol polymerization (n-bar) can then be calculated from the determined distribution of polyglycerol species in the sample according to the following equation:

$$n - bar = \frac{\sum_{n=1}^{\infty} n \times \frac{Wt \% G}{MW_{Gn}}}{\sum_{n=1}^{\infty} \frac{Wt \% G}{MW_{Gn}}}$$

where $Wt\%G_n$ = weight % of a polyglycerol ester species having n repeating units
$MW_{Gn}$ = the molecular weight of a polyglycerol ester species having n repeating units = $n(74)+18$ 2. % Esterification of Polyglycerol Ester Mixture The % esterification of a polyglycerol ester sample is the average degree of polyglycerol esterification expressed on a mole percent basis. The % esterification is calculated indirectly from the Saponification Value, the Acid Value and the average degree of glycerol polymerization of a polyglycerol ester sample. The analytical methods for determining the Saponification Value and the Acid Value of a polyglycerol ester sample are as hereinbefore described for determination of those values for polyol polyester materials in general. From the Saponification Value and the Acid Value, the "Ester Value" (EV) of the polyglycerol ester sample can then be calculated. The Ester Value of a given polyglycerol ester sample is the difference between the Saponification Value (SV) and the Acid Value (AV) of the sample.

From the Ester Value, the Corrected Ester Value is calculated. The "Corrected Ester Value" ($EV_{cor}$) of a given polyglycerol ester sample is the calculated ester value of a pure sample containing only the polyglycerol esters, i.e., containing no free fatty acid (ffa). Corrected Ester Value is calculated according to the following equation:

$$EV_{cor} = \frac{EV}{1 - \frac{\% ffa}{100}}$$

Next, the average degree of esterification (i-bar) is calculated from the corrected ester value and the average molecular weight of the polyglycerol ($MW_{Gn-bar}$). The average degree of esterification (i-bar) is a molar quantity which describes the average number of the hydroxyl groups of the polyglycerol ester which are esterified with fatty acids. Thus, $$i - bar = \frac{(EV_{cor})(MW_{Gn-bar})}{56{,}100 - (EV_{cor})(MW_{FA} - 18)}$$

where $MW_{Gn-bar} = n(74) + 18$
$MW_{FA}$ = the average molecular weight of the fatty acid ester groups (fa) present in the polyglycerol ester sample calculated from the weight percent fatty acids of the various species as measured by the GCFAC method hereinbefore described according to the equation:

$$\text{avg. } MW_{fa} = \Sigma \frac{wt. \% fa}{100} MW_{fa}$$

Lastly, the % esterification is calculated according to the following equation:

$$\% \text{ est.} = \frac{(i - bar)\ 100}{n - bar + 2}$$

VIII. Specific Examples

Preparation of the nondigestible fat compositions of the present invention is illustrated by the following examples:

EXAMPLE I

Preparation of Liquid Nondigestible Oil and Hardstock Components

Both the liquid nondigestible oil and hardstock components of nondigestible fat compositions are prepared by essentially completely esterifying sucrose with fatty acids from naturally occurring source oils. For the liquid nondigestible oil component cottonseed oil is used. For the sucrose polyester hardstock, soybean oil, hydrogenated to an Iodine Value of about 8 or less, is used.

Both liquid and hardstock are prepared by converting the fatty acids from the source oils to their methyl esters and by then reacting these methyl esters with sucrose at about 135° C. in the presence of a potassium carbonate catalyst and the potassium soap of the source oil used. The procedure employed is substantially similar to that described in Example 1 of Volpenhein, U.S. Pat. No. 4,517,360; Issued May 14, 1985.

The resulting sucrose polyesters have the fatty acid composition and ester distribution as set forth in Table I.

TABLE I

| Fatty Acid Content (%) | Liquid Sucrose Polyester | Solid Sucrose Polyester Hardstock |
|---|---|---|
| $C_{14}$ | 0.5 | — |
| $C_{16}$ | 20.4 | 9.6 |
| $C_{18}$ | 4.3 | 87.3 |
| $C_{18:1}$ | 32.6 | 1.5 |
| $C_{18:2}$ | 40.9 | 0.4 |
| $C_{18:3}$ | 0.2 | — |
| $C_{20}$ | 0.4 | |
| Other | 0.7 | 0.5 |
| Ester Distribution | | |
| % Octa | 78.4 | 92.5 |
| % Hepta | 21.3 | 7.5 |
| % Hexa | <0.1 | <0.1 |
| % Penta | 0.3 | <0.1 |
| % Lower | <0.1 | — |

EXAMPLE II

Preparation of Diversely Esterified Sucrose Polyester (Sunflower/$C_{22}$) Crystal Modifier This example describes the preparation of a diversely esterified sucrose polyester crystal modifier of this invention by a modification of the process described in hereinbefore referenced U.S. Pat. Nos. 4,518,772 and 4,517,360.

High erucic acid rapeseed oil (HEAR) is blended with low erucic acid rapeseed oil (LEAR) to a composition of 38% erucic acid. The rapeseed oil blend is mixed with 3%–6% refined, bleached cottonseed oil to obtain an oil composition having approximately 35% of $C_{22}$ acids (i.e., behenic plus erucic). This rapeseed/cottonseed stock is then hydrogenated to an Iodine Value less than 4. Hydrogenation is done with nickel catalyst levels typical of those used for any vegetable oil, using 0–100 psig pressure, and a temperature of approximately 375° F. The material is deodorized at a temperature of 375°–495° F. The hardened, deodorized rapeseed oil has the following characteristics: fatty acid composition: 3–7% $C_{16:0}$, 45–55% $C_{18:0}$, 0–2% $C_{18:1}$, 0–1% $C_{18:2}$, 4–8% $C_{20:0}$, 33–37% $C_{22:0}$, 0–1% $C_{22:1}$, 0–2% $C_{24:0}$. Free fatty acid content is 0.01–0.1% and Lovibond red color is about 1.0. The rapeseed/cottonseed oil is converted into methyl esters through an esterification process in which the oil is mixed with methanol, a sodium methoxide catalyst is added, and the reaction is continued until all the triglycerides are converted into methyl esters. By-product glycerine is settled by gravity after the reaction is completed. The esters are then water washed with hot water to remove trace levels of glycerine and soap. The water phase is settled out by gravity after each wash. The esters are flash distilled in a batch mode to both remove unsaponifiable materials and to obtain a more concentrated $C_{22}$ material. The distillation is done under a vacuum of 0.5–2 mm Hg and a temperature of 300°–410° F. The last 10%–15% of the esters distilled are collected into a clean vessel for use in making the desired sucrose polyester. The other 85–90% is discarded. The ester composition of the last 10–15% collected is: 4% $C_{18:0}$, 6% $C_{20:0}$, 87% $C_{22:0}$, 3% $C_{24:0}$. These are esters "A".

Refined and bleached sunflower oil is deodorized at a temperature of 375°–495° F. under vacuum. The deodorized sunflower oil has the following characteristics: Iodine Value: 125–140; fatty acid composition: 5–10% $C_{16:0}$, 2–6% $C_{18:0}$, 19–26% $C_{18:1}$, 63–74% $C_{18:2}$, 0–2% $C_{18:3}$, 0–1% $C_{20:0}$, 0–1% $C_{22:0}$. Free fatty acid content is 0.01–0.1% and Lovibond red color is about 1.3. The sunflower oil is converted into methyl esters through the same esterification process as described above. The esters are flash distilled in a batch mode, primarily to remove unsaponifiable materials. The distillation is done under a vacuum of 0.5–2.0 mm Hg and a temperature of 300°–410° F. These are esters "B".

About 70.5 Kg of methyl esters of refined soybean oil fatty acid, hardened to an IV of about 2, are mixed with 209 Kg of methanol and 15.4 Kg of potassium hydroxide in a stainless steel batch reactor. The mixture is heated to about 145° F. (63° C.) with agitation for 1 to 3 hours at atmospheric pressure. During this time, all but a residual amount of the methyl esters are saponified to make soap. About 1193.6 Kg of ester "A" is blended with 241.4 Kg of ester "B" to make ester blend "C". The ester composition of blend "C" is about: 1.2% $C_{16:0}$, 3.8% $C_{18:0}$, 3–8% $C_{18:1}$, 10.7% $C_{18:2}$, 4,7% $C_{20:0}$, 71.9% $C_{22:0}$, 3% $C_{24:0}$. About 545.5 Kg of ester "C" are added to the previously made soap mixture. About 104.5 Kg of granular sucrose is then added to give a 5:1 molar ratio of methyl ester to sucrose. Potassium carbonate is then added to the mixture (approx. 0.5 wt. percent of the reaction mix) to catalyze the transesterification. This mixture is agitated and slowly heated at atmospheric pressure until the temperature reaches about 275° F. (135° C.). This is to remove the methanol.

A vacuum is then pulled and the mixture agitated for up to 8 hours to form the mono-, di- and tri- sucrose esters. Small quantities of tetra- and pentaesters are also formed during this stage. Additional methyl ester "C" (890 Kg) which has been preheated to 275° F. (135° C.) is added to bring and maintain the molar ratio of the esters to sucrose to 14–15:1. Additional potassium carbonate is then added twice to the mixture (each addition being approximately 0.5 wt. percent of the initial reaction mix). When the reaction conditions stabilize at 275° F. (135° C.), a nitrogen sparge is used to improve agitation and promote methanol stripping. This second reaction stage lasts approximately 4 to 13 hours.

The reaction mixture is then cooled under nitrogen to between 149° F. (65° C.) and 185° F. (85° C.). The crude reaction mixture is agitated with about 91 Kg water. The hydrated crude reaction mixture is passed through a centrifuge to separate a heavy and a light phase. The heavy phase which contains the soaps, excess sugars and potassium carbonate is discarded. The light phase is then washed with an additional 264 Kg of water. The light phase, which contains methyl esters and the sucrose polyester is then dried to remove moisture at 170°–190° F. (76°–88° C.) under 70 mm Hg or less vacuum for 30 to 60 minutes. Filtrol 105 (1.0 wt. percent) is added and the mix is agitated at 167° F. (75° C.) to 190° F. (88° C.). The slurry is separated by filtration or other means until there is less than 0.1 wt. percent fines. The liquid is then passed through a 1 micron filter.

The refined and bleached reaction mix is then passed through a stainless steel wiped-film evaporator or other suitable equipment to distill off the bulk of the methyl esters. The distillation takes place at 392° F. (200° C.) to 455° F. (235° C.) under approximately 0.5 mm Hg of vacuum. The sucrose polyester is then deodorized by passing downward through a stainless steel packed column deodorizer or other suitable device at 392° F. (200° C.) to 450° F. (232° C.) under a vacuum of about <25 mm Hg. Steam is introduced to the bottom of the column and passes countercurrently to the sucrose polyester. Feed rates and temperature are adjusted until the methyl ester content of the sucrose polyester is below 1000 ppm. The mixture is then cooled to between 149° F. (65° C.) to 185° F. (85° C.) and passed through a 1 micron filter. Sucrose polyester made according to the foregoing procedure has the approximate composition and properties as set forth in Table II.

TABLE II

| Fatty Acid Composition | |
|---|---|
| $C_{16}$ | 1.2% |
| $C_{17}$ | 0 |
| $C_{16:1}$ | 0 |
| $C_{18}$ | 4.6 |
| $C_{18:1}$ | 3.7 |
| $C_{18:2}$ | 10.9 |
| $C_{18:3}$ | 0 |
| $C_{20}$ | 4.6 |
| $C_{20:1}$ | 0 |
| $C_{22}$ | 71.7 |
| $C_{22:1}$ | 0.2 |
| $C_{24}$ | 2.8 |
| Other | 0.4 |
| Iodine Value 22.4 | |
| Complete Melting Point 70.4° C. | |
| (By Differential Scanning Calorimetry) | |
| Ester Distribution | |
| Octa | 71.6% |
| Hepta | 28.2 |
| Hexa | 0.2 |
| Penta | <0.1 |
| Lower | <0.1 |

EXAMPLE III

Preparation of Diversely Esterified Sucrose Polyester ($2C_{12}$, $6C_{22}$) Crystal Modifier This example describes preparation of another type of diversely esterified sucrose polyester via an acid chloride synthesis route.

About 16 grams (0.047M) of sucrose (Colonial Baker's Special) is dissolved in 340 ml pyridine and 110 ml DMF at 50° C. for 1 hour. This solution is allowed to cool back to room temperature before addition of the acid chloride.

A blend of 20.4 grams (0.09M) of $C_{12}$ acid chloride in 55 ml n-heptane is prepared and charged into an addition funnel. This solution is slowly added to the stirring sucrose solution. With addition complete, the entire contents of the reactor are heated to 65° C. and held for ~6 hours. Heat is stopped after that time and agitation of the reaction mix is allowed to continue overnight at room temperature.

Thereafter, a blend of 102.0 grams (0.28M) of $C_{22}$ acid chloride in 100 ml n-heptane is prepared and slowly added to the reaction mix through the addition funnel. When addition is complete the reactor is again heated to 65° C. and held for ~5 hours. At the end of that time the heating source is stopped and agitation is allowed to continue overnight at room temperature.

Thereafter the reaction mix is again heated to 65° C. for 2 hours, then allowed to cool at room temperature. A blend of 2.0 grams (0.009M) of $C_{12}$ acid chloride, 10.0 grams (0.028M) of $C_{22}$ acid chloride in 50 ml of n-heptane is prepared and slowly added to the reaction mix when it reaches room temperature. This is allowed to run at room temperature overnight.

At this point, a cleanup sequence is started.
Cleanup

The entire contents of the reactor are transferred to a rotovap at which point the solvent is stripped leaving the crude reaction mix. 500 ml of methylene chloride is added to the evaporated crude and transferred to a large separatory funnel.

This is then washed:
3 times with 1000 ml of a warm saturated $NaCl/H_2O$ solution.
1 time with a 10% v:v warm $HCl:H_2O$ solution.
2 times with 1000 ml of a warm saturated $NaCl/H_2O$ solution.
1 time with 1000 ml of a warm $Ca(OH)2/H_2O$ solution having a pH of 13. Both the aqueous and solvent phase are passed through a Celite bed under vacuum.

The recovered solvent phase is washed 2 times with 1000 ml of warm saturated $NaCl/H_2O$ solution.

The solvent phase is then transferred to a clean Edenmeyer flask equipped with a magnetic stir bar. With agitation, magnesium sulfate and florisil are added to chemically dry and decolorize the material over a period of ~4 hours.

The magnesium sulfate/florisil are separated from the solvent phase by filtration. The solvent phase is then extracted two times with 500 ml of hot MeOH. Final traces of MeOH are evaporated from the solvent/product phase on the rotovap.

One-half of the product obtained (50.5 grams) is taken up in 100 ml ethyl acetate. At the same time 1000 ml of MeOH is charged into a large Edenmeyer flask equipped with a magnetic stir bar. The ethyl acetate/product solution is slowly poured into the stirring MeOH. Crystals form immediately and the entire solution is allowed to stir for 2 hours.

The product crystals are filtered away from the mother liquor using a vacuum equipped Buchner funnel. During this step the crystals are rinsed with MeOH.

The crystals are transferred to a glass drying dish and allowed to air dry (remove MeOH) overnight.

Analytical results are obtained for this product are set forth in Table III.

TABLE III

| Fatty Acid Composition % | |
|---|---|
| $C_{10}$ | 0.1 |
| $C_{12}$ | 10.5 |
| $C_{14}$ | 0.4 |
| $C_{16}$ | 0.1 |
| $C_{18}$ | 1.1 |
| $C_{18:1}$ | 0.1 |
| $C_{20}$ | 3.0 |
| $C_{22}$ | 82.0 |
| $C_{22:1}$ | 0.4 |
| $C_{24}$ | 2.1 |
| Iodine Value = 0.5 | |
| % Octa by HPLC = 87.0% | |

EXAMPLE IV

Preparation of Diversely Esterified Sucrose Polyester ($1C_{12}$, $7C_{22}$) Crystal Modifier This example demonstrates preparation of another type of diversely esterified sucrose polyester via an acid chloride synthesis route:

| Raw Materials: | |
|---|---|
| Sucrose | Colonial Bakers Special |
| $C_{12}$ acid chloride | Prepared from pure $C_{12}$ fatty acid |
| $C_{22}$ acid chloride | Prepared from behenic acid |

-continued

| | |
|---|---|
| heptane | Fisher brand |

Preparation Procedure 1. 30 gms sucrose are dissolved into a mixture of 100 ml pyridine and 120 ml DMF. The solution is transferred into a reaction flask.
2. 21.0 gm $C_{12}$ acid chloride are then diluted into 50 ml heptane.
3. The apparatus is assembled with heating mantle, overhead stirrer, mercury thermometer, cold water condenser ($CaSO_4$ tube), $N_2$ inlet and addition funnel.
4. The $C_{12}$ acid chloride solution is transferred into the addition funnel and is then slowly added to the sucrose solution. The reaction is allowed to proceed ~1 hour.
5. 241.7 gm $C_{22}$ acid chloride are then diluted into 200 ml heptane. This solution is transferred into the addition funnel and is slowly added to the reaction flask.
6. The contents of the flask are then heated to ~90° C., and the reaction is allowed to continue ~3 hours (cooled to room temperature overnight).
7. The reaction is continued at 70° C. for ~10 hours.
8. The crude reaction mixture is then subjected to cleanup procedures substantially similar to those described hereinbefore in Example III. The crystals recovered are analyzed with the analytical results set forth in Table IV.

TABLE IV

| Fatty Acid Composition % | |
|---|---|
| $C_{12}$ | 7.81 |
| $C_{16}$ | 0.23 |
| $C_{18}$ | 1.47 |
| $C_{18:1}$ | 0.08 |
| $C_{18:2}$ | 0.15 |
| $C_{20}$ | 4.30 |
| $C_{22}$ | 82.87 |
| $C_{24}$ | 0.94 |
| Other | 2.16 |
| % Octa ester = 87.5 | |

EXAMPLE V

Preparation of Diversely Esterified Sucrose Polyester ($C_{22}$-Toluic) Crystal Modifier This example describes preparation of another type of diversely esterified sucrose polyester containing aromatic ester groups.

Behenic Methyl Ester Preparation

Behenic methyl esters are prepared from hydrogenated high erucic rapeseed oil. About 870 grams of hydrogenated high erucic rapeseed oil, about 174 grams of methanol, and about 12.2 grams of sodium methoxide solution (25% in methanol) are added to a spherical 3-liter glass reactor. The reactor has a heating mantle, thermometer, temperature controller, reflux condenser, variable speed agitator, vacuum take-off, and bottom outlet. The mixture is reacted at about 65° C. for approximately 1.5 hours, while refluxing the methanol. The agitation is stopped, and the glycerin by-product of the rapeseed oil is allowed to settle for about 30 minutes. The glycerin settles to the bottom of the reactor, and is removed through the bottom outlet. About 30 additional grams of methanol, and about 5.2 grams of sodium methoxide solution (25% in methanol) are added to the glass reactor, and the mixture is reacted at about 65° C. for about 30 minutes. The agitation is stopped, the glycerin is settled for about 30 minutes, and removed through the bottom outlet. About 100 grams of water are added to the mixture, stirred, allowed to settle, and removed through the bottom outlet. The water-washing procedure is repeated two more times. The reflux condenser is removed, and vacuum is applied to the reactor, and the residual water and methanol are evaporated. The vacuum is broken, and a glass fractionation column is added to the reactor. The reactor is heated to about 170°–200° C. under a vacuum of about 0.3–1.0 mm Hg. Approximately 50% of the first material to evaporate from the column is collected and discarded. The next 40% (approximately) of material to evaporate from the column is collected as product. This product is approximately 92% by weight methyl behenate.

Sucrose Esterification

About 21.2 grams of methyl o-toluate (Aldrich Chemical Company) are mixed with about 366.2 grams of the behenic methyl esters. The molar ratio of toluic to behenic is about 1:7. About 152.6 grams of this methyl ester mixture are mixed in a 1-liter glass reactor along with about 34.4 grams of powdered sucrose, about 24 grams of powdered potassium stearate and about 1.4 grams of powdered potassium carbonate. The reactor has a heating mantle, thermometer, temperature controller, variable speed agitator, vacuum take-off, and bottom outlet. The mixture is agitated and heated at about 135° C. at about 15 mm Hg vacuum for about 1.5 hours. After about 1.5 hours, the vacuum is broken with nitrogen, and the remaining 234.8 grams (approximately) of the methyl ester mixture, along with about 1.4 grams of potassium carbonate are added to the reaction mixture. This mixture is reacted at about 135° C. under about 0.5–5.8 mm Hg for about 5 hours. The mixture is cooled to about 75° C., and about 30 grams of water are added to the mixture. The mixture is transferred to jars and centrifuged (Fischer Scientific Model Marathon 10 k Centrifuge) at about 2500 RPM for about 2 minutes. The liquid in the jars is then decanted from the soap layer at the bottom of the jars. About 5 grams of silica are added to the decanted liquid, and the mixture is stirred for about 30 minutes at about 75° C. The mixture is then filtered through filter paper using a Buchner funnel. The flitrate is then fed through a Pope 2-inch diameter wiped film evaporator at approximately 30 grams/hour to distill the unreacted methyl esters. The evaporator operates at about 235° C. under about 0.05–0.08 mm Hg. The product is then collected from the evaporator and cooled to ambient temperature.

This diversely esterified sucrose polyester product has a complete melting point of 70.5° C. (as measured by DSC described in the Analytical Methods section hereinbefore) and is 99.0% esterified. Other characteristics are set forth in Table V.

TABLE V

| Fatty Acid | % |
|---|---|
| $C_{14}$ | — |
| $C_{16}$ | 0.1 |
| $C_{18}$ | 2.0 |
| $C_{18:1}$ | — |
| $C_{18:2}$ | 0.2 |
| $C_{18:3}$ | — |
| $C_{20}$ | 7.8 |
| $C_{22}$ | 88.4 |

TABLE V-continued

| | % |
|---|---|
| $C_{24}$ | 0.1 |
| Toluic | 1.4 |
| Other | — |
| Ester Distribution | |
| Octa | 92.9 |
| Hepta | 6.7 |
| Hexa | 0.4 |
| Lower | — |

EXAMPLE VI

Preparation of Sucrose Polyester Dimer Crystal Modifier

This example describes preparation of yet another type of crystal modifier material in the form of sucrose polyester material prepared from behenic methyl esters and methyl esters of dimerized oleic acid.

Behenic Methyl Ester Preparation

Behenic methyl esters are prepared in the same general manner as described hereinbefore in Example V. They have the fatty acid composition as set forth hereinafter in Table VI.

Dimer Methyl Ester Preparation

About 100 grams of dimer fatty acids prepared from fractionated, distilled tallow fatty acids (Henkel 1008 dimer fatty acid) are added to a 1-liter glass reactor along with about 300 ml of Supelco BF3 (boron trifluoride)/methanol solution. The reactor is agitated with a paddle stirrer, has a heating mantle with temperature controller, a thermometer, an addition funnel, and a water-cooled reflux condenser. The temperature of the reactor is raised to about 65°-70° C., and kept there for about 2 hours. At the end of about 2 hours, an additional 100 ml of BF3/methanol is added to the mixture, dropwise, through the addition funnel over the course of about an hour. The mixture is transferred to a large separation funnel and the phases are allowed to separate. The methanol layer is removed, then about 50 grams of hexane is added to the mixture in the separation funnel and mixed thoroughly. This mixture is washed with about 50 grams of distilled water, the water layer is allowed to separate, and then removed. The water-washing procedure is repeated two more times. The mixture in the separatory funnel is transferred to a rotary evaporator, and the hexane is evaporated from the methyl esters. A base titration of the dried methyl esters is performed to ensure that the free fatty acid level is less than about 5%. The methyl esters are then run through a silica column to remove the remaining free fatty acid. The fractionated distilled tallow fatty acids from which the dimer fatty acids and, subsequently, the dimer methyl esters, are prepared typically have the compositions set forth hereinafter in Table VI.

Sucrose Esterification

About 72.8 grams of the dimer methyl esters are mixed with about 306.3 grams of the behenic methyl esters. The ratio of dimer fatty acids: $C_{22}$ is about 1:7. About 189.5 grams of this methyl ester mixture are added to a 1-liter spherical glass reactor along with about 34.4 grams of powdered sucrose, about 24 grams of powdered potassium stearate and about 1.4 grams of powdered potassium carbonate. The reactor has a heating mantle, thermometer, temperature controller, variable speed agitator, vacuum take-off, and bottom outlet. The mixture is agitated and heated at about 135° C. at about 15 mm Hg vacuum for about 1.5 hours. After about 1.5 hours, the vacuum is broken with nitrogen, and the remaining 189.6 grams (approximately) of the methyl ester mixture, along with about 1.4 grams of potassium carbonate are added to the reaction mixture. This mixture is reacted at about 135° C. under about 0.5–5.1 mm Hg vacuum for about 5 hours. The mixture is cooled to about 75° C., and about 30 grams of water are added to the mixture. The mixture is transferred to jars and centrifuged (Fischer Scientific Model Marathon 10K Centrifuge) at about 2500 RPM for about 2 minutes. The liquid in the jars is then decanted from the soap layer at the bottom. About 5 grams of silica are added to the decanted liquid, and the mixture is stirred for about 30 minutes at about 75° C. The mixture is then filtered through filter paper using a Buchner funnel. The filtrate is then fed through a Pope 2-inch diameter wiped film evaporator at approximately 30 grams/hour to distill the unreacted methyl esters. The evaporator operates at about 235° C. under about 0.04–0.05 mm Hg. The product is then collected from the evaporator and cooled to ambient temperature.

The resulting solid sucrose polyester crystal modifier product is about 53.0% polymer and about 47% monomer. The polymer material comprises about 19.8% dimer, about 11.8% trimer and about 21.4% tetramer and higher. 16.8% of the product is octaester. Additional information concerning this crystal modifier product is set forth in Table VI.

TABLE VI

| FATTY ACID CONTENT | BEHENIC METHYL ESTERS (%) | TALLOW (%) | SOLID SUCROSE POLYESTER CRYSTAL MODIFIER (%) |
|---|---|---|---|
| $C_{14}$ | — | 6.0 | — |
| $C_{16}$ | 0.88 | 11.0 | 0.45 |
| $C_{18}$ | 1.4 | <1.0 | 1.65 |
| $C_{18:1}$ | — | 73.0 | — |
| $C_{18:2}$ | — | 8.0 | — |
| $C_{18:3}$ | — | 1.0 | — |
| $C_{20}$ | 4.37 | — | 6.61 |
| $C_{22}$ | 91.66 | — | 82.54 |
| $C_{24}$ | 1.53 | — | 0.08 |
| Dimer fatty acid | — | — | 8.30 |
| Other | — | 1.0 | 0.20 |

EXAMPLE VII

A polyglycerol ester material suitable for use as a crystal modifier is prepared by modifying a narrow distribution (n-bar=3.19) commercially available polyglcyerol ester (PGE) product. In such a procedure Triodan 55 (Lot #00202, Grinsted Denmark) is fractionated to remove most of the monoesters and some of the diesters leaving mostly di-, tri- and tetraesters with small amounts of penta- through heptaester. The starting polyglycerol ester has an i-bar of 1.30 and a degree of esterification of 25%.

The resulting solid polyglycerol ester has the attributes set forth in Table VII.

TABLE VII

| Saponification Value: | 159.4 |
|---|---|
| Acid Value: | 0.6 |
| Corrected Ester: | 159.3 |
| n-bar: | 3.54 |
| i-bar: | 2.83 |
| Melting point: | 56.2° C. |
| Degree of Esterification: | 51.1% |

TABLE VII-continued

| MWfa | 271.2 |
|---|---|
| Fatty Acid Composition: | % |
| $C_{12}$ | 0.1 |
| $C_{14}$ | 1.2 |
| $C_{15}$ | 0.1 |
| $C_{16:0}$ | 41.2 |
| $C_{16:1}$ | 0.2 |
| $C_{17}$ | 0.3 |
| $C_{18:0}$ | 55.6 |
| $C_{18:1}$ | 0.2 |
| $C_{18:2}$ | 0.2 |
| $C_{20}$ | 0.7 |

EXAMPLE VIII

A number of nondigestible fat compositions are prepared by combining the liquid nondigestible oil and sucrose polyester hardstock as described in Example I with the several crystal modifier species described in Example II through Example VII. To prepare such compositions, the liquid sucrose polyester, the sucrose polyester hardstock and the crystal modifier material are mixed and heated until all the solids in the mixture are dissolved. The mixture is then cooled back to room temperature at a rate of 37.3° F./min. Such cooling brings about crystallization of solid sucrose polyester material in the form of small platelet-like particles which are dispersed in the liquid nondigestible oil. Table VIII describes the characteristics of each such composition in greater detail. Table VIII also identifies the Figure in the set of photomicrographs which represents each such composition.

TABLE VII

| Composition Number | Liquid Oil | Sucrose Polyester Hardstock | Crystal Modifier | Hardstock/ Modifier Ratio | % Solids in Composition | Average Particle Thickness | SFC Profile Slope | Photo- Micro- FIG. No. |
|---|---|---|---|---|---|---|---|---|
| A | C16/C10 sucrose octaester Ex. I | C18 sucrose octaester Ex. I | Sunflower/C22 - Ex. II | 6:4 | 3 | ≦50 mm | NA | 3 |
| B | C16/C10 sucrose octaester Ex. I | C18 sucrose octaester Ex. I | 2-C12/6-C22 - Ex. III | " | 3 | ≦50 mm | NA | 4 |
| C | C16/C10 sucrose octaester Ex. I | C18 sucrose octaester Ex. I | 1-C12/7-C22-Ex. IV | " | 3 | ≦50 mm | NA | 5 |
| D | C16/C10 sucrose octaester Ex. I | C18 sucrose octaester Ex. I | C22/Toluic - Ex. V | " | 9 | NA | 0 | 6 |
| E | C16/C10 sucrose octaester Ex. I | C18 sucrose octaester Ex. I | C22/Dimer - Ex. V | " | 9 | NA | 0 | 7 |
| F | C16/C10 sucrose octaester Ex. I | C18 sucrose octaester Ex. I | PGE - Ex. VI | " | 9 | NA | −0.1 | 8 |
| G | C16/C10 sucrose octaester Ex. I | C18 sucrose octaester Ex. I | Monobehenin (A) | " | 9 | NA | −0.1 | 9 |
| H | C16/C10 sucrose octaester Ex. I | C18 sucrose octaester Ex. I | Beeswax (B) | " | 9 | NA | −0.1 | 10 |

(A) Monobehenin is obtained from Grinsted (Lot #TSR D31).
(B) Beeswax is obtained from Aldrich #24, 322-1 (bleached white).

EXAMPLE X

Norchip potatoes are used which have been sliced to a thickness of about 0.052 inches (0.13 cm). The sliced potatoes are fried in a 5-pound batch fryer at a temperature of 365° F. (185° C.) for 3 minutes. Approximately 225 potato chips are fried in each of the fat compositions of Examples VIII(A) through VIII(H).

Ingestion of these potato chips which have absorbed the nondigestible fat compositions in which they were fried will not result in passive oil loss, and the potato chips are not unacceptably waxy tasting.

What is claimed is:

1. A nondigestible fat composition useful as a replacement for triglyceride fats or oils in foods, which fat composition has a Solid Fat Content profile slope between 70° F. and 98.6° F. of from 0 to about −0.75 and which fat composition comprises:
   A. a liquid nondigestible oil having a complete melting point below about 37° C.; and
   B. nondigestible solid particles dispersed in said oil in an amount sufficient to control passive oil loss upon ingestion of said composition, said particles having
      i) a complete melting point above about 37° C.; and
      ii) a thickness of about 1 micron or less;
   said particles further consisting essentially of a cocrystallized blend of:
      (x) a nondigestible solid polyol fatty acid polyester hardstock having a complete melting point above about 37° C. and normally tending to form spherulitic particles having a diameter of about 3 microns or larger when crystallized in said oil; and
      (y) a crystal modifier capable of inducing said hardstock to form solid nondigestible platelet-like particles having a thickness of about 1 micron or less when cocrystallized with said hardstock in the presence of said liquid nondigestible oil;
   the ratio of said hardstock to said crystal modifier in said cocrystallized blend ranging from about 95:5 to about 20:80.

2. A nondigestible fat composition according to claim 1 which comprises from about 60 to about 99% liquid nondigestible oil and from about 1 to about 40% of the nondigestible solid particles dispersed in said oil.

3. A nondigestible fat composition according to claim 2 wherein

A) the solid polyol polyester hardstock is derived from a sugar or sugar alcohol having from 6 to 8 hydroxyl groups;

B) the crystal modifier induces the formation of nondigestible particles having a thickness of about 0.1 micron or less; and C) the ratio of hardstock to crystal modifier in the cocrystallized blend ranges from about 80:20 to 20:80.

4. A nondigestible fat composition according to claim 3 wherein the crystal modifier is selected from A) diversely esterified polyol polyesters wherein at least 15% of the ester groups therein are formed from $C_{20}$ or higher saturated fatty acid radicals;

B) polyol polyester materials comprising from about 1% to 100% of a polyol polyester polymer component wherein at least 15% of the hydroxyl groups of said polyol polyester material are esterified with $C_{20}$ or higher saturated fatty acid radicals;

C) polyglycerol esters containing at least 2 glycerol moieties and having at least 30% of the hydroxyl groups of said glycerol moieties esterified with $C_{18}$ or higher fatty acid radicals;

D) naturally occurring waxes and paraffinic hydrocarbon microcrystalline waxes;

E) monoglycerides containing one ester group derived from $C_{18}$ or higher fatty acid radicals; and F) long chain alcohols.

5. A nondigestible fat composition according to claim 4 wherein the liquid nondigestible oil is a liquid sucrose fatty acid polyester.

6. A nondigestible fat composition according to claim 5 having a Solid Fat Content profile slope between 70° F. and 98.6° F. of from 0 to about −0.5% solids/°F.

7. A nondigestible fat composition according to claim 6 wherein the crystal modifier comprises a diversely esterified polyol polyester containing dissimilar ester groups selected from A) unsaturated fatty acid radicals containing at least 12 carbon atoms;

B) saturated fatty acid radicals containing from 2 to 12 carbon atoms;

C) fatty-fatty acid radicals comprising an hydroxyl group-containing radical of 12 to 22 carbon atoms wherein another radical of 12 to 22 carbon atoms is esterified onto said hydroxyl group; and D) aromatic and branched chain radicals.

8. A nondigestible fat composition according to claim 7 wherein the crystal modifier is selected from sucrose tetrabehenate tetracaprylate, sucrose pentabehenate trilaurate, sucrose hexabehenate dicaprylate, sucrose hexabehenate dilaurate, the sucrose octaester of oleic and behenic fatty acid radicals in a 2:6 molar ratio, the sucrose octaester of lauric, linoleic and behenic fatty acid radicals in a 1:3:4 molar ratio, and the sucrose hepta- and octaesters of $C_{18}$ mono- and/or di-unsaturated fatty acid radicals and behenic fatty acid radicals in a molar ratio of unsaturated to behenic acid radicals of about 1:7 to 3:5.

9. A nondigestible fat composition according to claim 6 wherein the crystal modifier is a polymer-containing sucrose polyester material comprising from about 50% to 100% of a sucrose fatty acid polyester polymer component and from 0% to about 50% of a sucrose fatty acid polyester monomer component, wherein at least about 90% of the sucrose polyester material is esterified with $C_{20}$ to $C_{24}$ saturated fatty acid radicals.

10. A nondigestible fat composition according to claim 9 wherein the crystal modifier comprises sucrose polyester material esterified with dimerized oleic acid radicals and behenic acid radicals.

11. A nondigestible fat composition according to claim 6 wherein the crystal modifier is a polyglycerol ester material having an average degree of glycerol polymerization of from about 3 to 6 and having at least about 50% of the hydroxyl groups esterified with $C_{16}$ to $C_{24}$ fatty acid radicals.

12. A nondigestible fat composition useful as a replacement for triglyceride fats or oils in foods, which fat composition has a Solid Fat Content profile slope between 70° F. and 98.6° F. of from 0 to about −0.75 and which fat composition comprises:

A) a liquid nondigestible oil comprising sucrose fatty acid polyester material having a complete melting point below about 37° C.; and B) nondigestible solid particles dispersed in said oil in an amount sufficient to control passive oil loss upon ingestion of said composition, said particles having
i) a complete melting point above about 37° C.; and
ii) a thickness of about 0.1 micron or less;

said particles further consisting essentially of a cocrystallized blend of:

a) sucrose polyester hardstock having a complete melting point above about 37° C.; and b) a crystal modifier selected from i) the sucrose hepta and octaesters of oleic and behenic acids in a molar ratio of from about 1:7 to 5:3;

ii) the sucrose hepta and octaesters of lauric and behenic acids in a molar ratio of from about 1:7 to 5:3;

iii) the sucrose hepta and octaesters of dimerized oleic acid and behenic acid in a molar ratio of from about 1:7 to 5:3; and iv) polyglycerol esters having an average degree of glycerol polymerization of from about 3 to 6 and having at least about 50% of the hydroxyl groups esterified with $C_{18}$ to $C_{24}$ saturated fatty acid radicals;

the ratio of hardstock to crystal modifier in said cocrystallized blend ranging from about 80:20 to 60:40; wherein the liquid nondigestible oil and the nondigestible cocrystallized blend of hardstock and crystal modifier are co-crystallized in a manner such that the nondigestible solid forms dispersed platelet-like particles having a thickness of 0.1 micron or less in the liquid nondigestible oil.

13. A food product comprising from about 10% to 100% of the nondigestible fat composition of claim 1.

14. A process for preparing a nondigestible fat composition useful as a replacement for triglyceride fats or oils in foods, which process comprises I) forming a melted mixture comprising:

A. a liquid nondigestible oil having a complete melting point below about 37° C.; and B. a cocrystallizable blend consisting essentially of:

(i) a nondigestible solid polyol fatty acid polyester hardstock having a complete melting point above about 37° C. and normally tending to form spherulitic particles having a size of about 3 microns or larger when crystallized in the oil; and (ii) a crystal modifier capable of inducing the hardstock to form nondigestible particles having a diameter or thickness of about 1 micron or less when cocrystallized with said hardstock in said oil;

the ratio of hardstock to crystal modifier in said cocrystallizable blend ranging from about 95:5 to about 20:80; and II) cooling the melted mixture formed in Step I in the presence of said liquid nondigestible oil in a manner such that the cocrystallizable blend forms nondigestible platelet-like particles dispersed in the liquid nondigestible oil to thereby provide said fat composition having a Solid Fat Content profile slope between 70° F. and 98.6° F. of from 0 to about −0.75; said nondigestible particles having
  i) a complete melting point above about 37° C., and
  ii) a thickness of about 1 micron or less;

said nondigestible particles being dispersed in said composition in an amount which is sufficient to control passive oil loss upon ingestion of said composition.

15. A process according to claim 14 wherein the composition prepared comprises from about 60 to about 99% liquid nondigestible oil and from about 1 to about 40% of the nondigestible solid particles dispersed in said oil.

16. A process according to claim 15 wherein
  A) the solid polyol polyester hardstock is derived from a sugar or sugar alcohol having from 6 to 8 hydroxyl groups;
  B) the crystal modifier induces the formation of nondigestible particles having a thickness of about 0.1 micron or less; and
  C) the ratio of hardstock to crystal modifier in the cocrystallizable blend ranges from about 95:5 to 25:75.

17. A process according to claim 16 wherein the crystal modifier is selected from
  A) diversely esterified polyol polyesters wherein at least 15% of the ester groups therein are formed from $C_{20}$ or higher saturated fatty acid radicals;
  B) polyol polyester materials comprising from about 1% to 100% of a polyol polyester polymer component wherein at least 15% of the hydroxyl groups of said polyol polyester material are esterified with $C_{20}$ or higher saturated fatty acid radicals;
  C) polyglycerol esters containing at least 2 glycerol moieties and having at least 30% of the hydroxyl groups of said glycerol moieties esterified with $C_{18}$ or higher fatty acid radicals;
  D) naturally occurring waxes and paraffinic hydrocarbon microcrystalline waxes;
  E) monoglycerides containing one ester group derived from $C_{18}$ or higher fatty acid radicals; and
  F) long chain alcohols.

18. A process according to claim 17 wherein the liquid nondigestible oil is a liquid sucrose fatty acid polyester.

19. A process according to claim 18 wherein the composition prepared has a Solid Fat Content profile slope between 70° F. and 98.6° F. of from 0 to about −0.5% solids/°F.

20. A process according to claim 19 wherein the crystal modifier is selected from
  A) the sucrose hepta and octaesters of oleic and behenic acids in a molar ratio of from about 1:7 to 5:3;
  B) the sucrose hepta and octaesters of lauric and behenic acids in a molar ratio of from about 1:7 to 5:3;
  C) the sucrose hepta and octaesters of dimerized oleic acid and behenic acid in a molar ratio of from about 1:7 to 5:3;
  D) polyglycerol esters having an average degree of glycerol polymerization of from about 3 to 6 and having at least about 50% of the hydroxyl groups esterified with $C_{18}$ to $C_{24}$ saturated fatty acid radicals.

21. A thickened digestible oil product comprising
  A) a liquid digestible triglyceride oil; and
  B) from about 2% to 20% of nondigestible solid particles dispersed in said digestible triglyceride oil; said nondigestible solid particles having a complete melting point above about 37° C. and a thickness of 1 micron or less; said particles further consisting essentially of a cocrystallized blend of:
    (i) a nondigestible solid polyol fatty acid polyester hardstock having a complete melting point above about 37° C. and normally tending to form spherulitic particles having a diameter of about 3 microns or larger when crystallized in said digestible oil; and
    (ii) a crystal modifier capable of inducing said hardstock to form nondigestible particles having a thickness of about 1 micron or less when cocrystallized with said hardstock in said digestible oil;
  the ratio of said hardstock to said crystal modifier in said cocrystallized blend ranging from about 95:5 to about 20:80; and wherein the liquid nondigestible oil and the nondigestible cocrystallized blend of hardstock and crystal modifier are co-crystallized in a manner such that the nondigestible solid forms dispersed platelet-like particles having a thickness of 1 micron or less in the liquid non-digestible oil.

22. A nondigestible fat composition useful as a replacement for triglyceride fats or oils in foods, which fat composition has a Solid Fat Content profile slope between 70° F. and 98.6° F. of from 0 to about −0.75 and which fat composition comprises:
  A. a liquid nondigestible oil having a complete melting point below about 37° C.; and
  B. nondigestible solid particles dispersed in said oil in an amount sufficient to control passive oil loss upon ingestion of said composition, said particles having
    i) a complete melting point above about 37° C.; and
    ii) a thickness of about 1 micron or less;
  said particles further consisting essentially of a cocrystallized blend of
    (x) a nondigestible solid polyol fatty acid polyester hardstock having a complete melting point above about 37° C. and normally tending to form spherulitic particles having a diameter of about 3 microns or larger when crystallized in said oil; and
    (y) a crystal modifier capable of inducing said hardstock to form nondigestible particles having a thickness of about 1 micron or less when cocrystallized with said hardstock in said oil;
  the ratio of said hardstock to said crystal modifier in said cocrystallized blend ranging from about 99.9:0.1 to about 20:80; and wherein the liquid nondigestible oil and the nondigestible cocrystallized blend of hardstock and crystal modifier are co-crystallized in a manner such that the nondigestible solid forms dispersed platelet-like particles having a thickness of 1 micron or less in the liquid non-digestible oil.

23. A nondigestible fat composition according to claim 22 which comprises from about 60 to about 99% liquid digestible oil and from about 1 to about 40% of the nondigestible solid particles dispersed in said oil.

24. A nondigestible fat composition according to claim 23 wherein
   A) the solid polyol polyester hardstock is derived from a sugar or sugar alcohol having from 6 to 8 hydroxyl groups;
   B) the crystal modifier induces the formation of nondigestible particles having a thickness of about 0.1 micron or less.

25. A nondigestible fat composition according to claim 24 wherein the crystal modifier is prepared via acid chloride synthesis.

* * * * *